(12) United States Patent
Ashley et al.

(10) Patent No.: US 6,815,463 B2
(45) Date of Patent: Nov. 9, 2004

(54) LAULIMALIDE DERIVATIVES

(75) Inventors: Gary Ashley, Alameda, CA (US); Brian Metcalf, Moraga Town, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 10/364,111

(22) Filed: Feb. 10, 2003

(65) Prior Publication Data

US 2003/0195181 A1 Oct. 16, 2003

Related U.S. Application Data

(63) Continuation of application No. 10/071,839, filed on Feb. 8, 2002, now Pat. No. 6,670,389.
(60) Provisional application No. 60/267,603, filed on Feb. 9, 2001.

(51) Int. Cl.[7] .................. C07D 417/06; C07D 493/08; C07D 493/18; A61K 31/335
(52) U.S. Cl. .............. 514/450; 514/451; 514/452; 514/453; 514/456; 514/560; 540/488; 549/267; 549/268; 549/269; 549/270; 549/271
(58) Field of Search .................. 540/488; 549/267, 549/268, 269, 270, 271; 514/450, 451, 452, 453, 456, 560

(56) References Cited

U.S. PATENT DOCUMENTS 6,414,015 B1  7/2002  Mooberry et al. .......... 514/455

FOREIGN PATENT DOCUMENTS

WO  WO 97/10242  3/1997
WO  WO 01/54689  8/2001

OTHER PUBLICATIONS

Corley et al., J. Org. Chem. (1988) 53:3644–3646.
Enev et al., J. Am. Chem. Soc. (2001) 123:10764–10765.
Ghosh et al., J. Am. Chem. Soc. (2000) 122:11027–11028.
Ghosh et al., J. Org. Chem. (2001) 66:8973–8982.
Jefford et al., Tetrahedron Letts. (1996) 37:159–162.
Mooberry et al., Cancer Res. (1999) 59:653–660.
Paterson et al., Org. Letts. (2001) 3(20):3149–3152.
Quinoa et al., J. Org. Chem. (1988) 53:3642.
Pryor, et al., "The Microtubule Stabilizing Agent Laulimalide Does Not Bind in the Taxoid Site, Kills Cells Resistant to Paclitaxel and Epothilones, and May not Require Its Epoxide Moiety for Activity," *Biochemistry* (2002) vol. 41, No. 29, 9109–9115.

*Primary Examiner*—Bruck Kifle
(74) *Attorney, Agent, or Firm*—Morrison & Foerster LLP

(57) ABSTRACT

Laulimalide compounds, intermediates thereto and methods for their preparation, and methods for their use in the treatment of diseases characterized by cellular hyperproliferation.

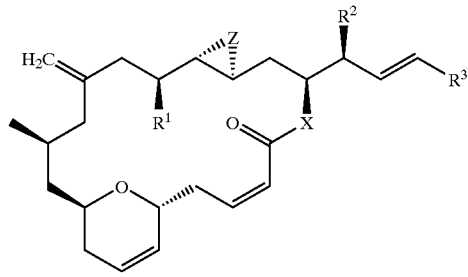

2 Claims, No Drawings

LAULIMALIDE DERIVATIVES

CROSS-REFERENCE TO RELATED APPLICATIONS

This application is a continuation of U.S. utility patent application Ser. No. 10/071,839, filed 8 Feb. 2002, now U.S. Pat. No. 6,670,389, which claims the benefit of U.S. provisional application Serial No. 60/267,603 filed 9 Feb. 2001, both all of which are incorporated herein by reference in their entireties.

BACKGROUND

Laulimalide (1) and isolaulimalide (2), also known as fijianolides, were originally isolated as cytotoxic agents from the Indonesian sponge *Hyatella* sp. (E. Quinoa et al., "Fijianolides, polyketide heterocycles from a marine sponge," *J. Org. Chem.*, 1988, 53, 3642; D. G. Corley et al., "Laulimalides. New potent cytotoxic macrolides from a marine sponge and a nudibranch predator," *J. Org. Chem.* 1988, 53, 3644–3646), and later found along with neolaulimalide (3) in the Okinawan sponge *Fasciospongia rimosa* (Jefford et al., "Structures and absolute configurations of the marine toxins, latrunculin A and laulimalide," 1996, *Tetrahedron Letts.* 37: 159–162; Higa et al., "Three new cytotoxic macrolides from a marine sponge," PCT publication No. WO 97/10242). The absolute structure of natural (−)-laulimalide has been determined by X-ray crystallography.

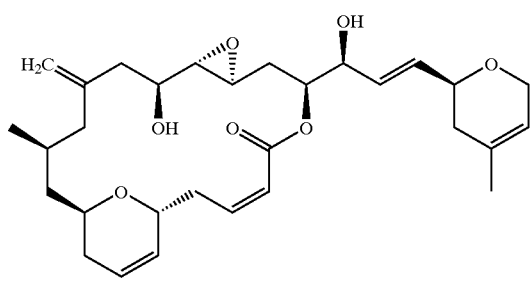

(−)-Laulimalide(1)
(fijianolide B)

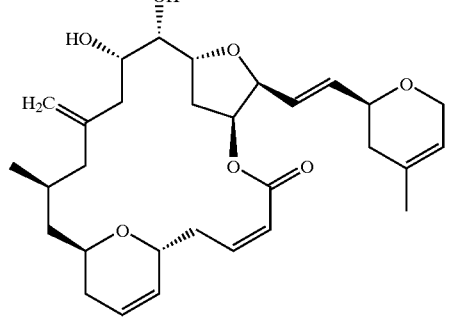

isolaulimalide(2)
(fijianolide A)

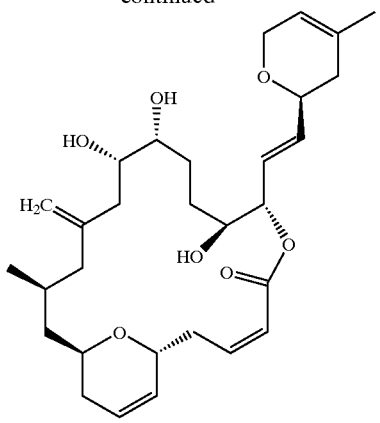

Neolaulimalide(3)

A number of total syntheses of laulimalide have been reported. See Ghosh et al., 2001, "Total synthesis of microtubule-stabilizing agent (−)-laulimalide," *J. Org. Chem.* 66: 8973–8982; Paterson et al., 2001, "Total synthesis of microtubule-stabilizing agent (−)-laulimalide," *Org. Letts.*: 3149–3152; Enev et al., 2001, "Macrocyclization via allyl transfer: total synthesis of laulimalide," *J. Am. Chem. Soc.* 123: 10764–10765; Ghosh et al., 2000, "Total synthesis of (−)-laulimalide," *J. Am. Chem. Soc.* 122: 11027–11028.

A mechanism-based screening program aimed at isolating novel microtubule-directed anticancer agents revealed both laulimalide and isolaulimalide to be potent stabilizers of microtubules, similar to paclitaxel. See S. Mooberry et al., 1999, *Cancer Res.*, 59, 653–660; Mooberry & Davidson, "Laulimalide compounds as microtubule stabilizing agents," PCT Publication No. WO 01/54689, incorporated herein by reference.

Because of the problems associated with the use of paclitaxel such as low solubility and resistance, there is an increasing need for alternative anti-cancer compounds. The present invention provides such compounds.

DETAILED DESCRIPTION OF THE INVENTION

The present invention provides laulimalide compounds, intermediates thereto and methods for their preparation, and methods for their use in the treatment of diseases characterized by cellular hyperproliferation.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Listed below are definitions of various terms used to describe this invention. These definitions apply to the terms as they are used throughout this specification, unless otherwise limited in specific instances, either individually or as part of a larger group.

The term "alkyl" refers to optionally substituted straight, branched or cyclic hydrocarbons comprising no unsaturation. "Alkenyl" refers to an optionally substituted straight, branched, or cyclic chain hydrocarbon with at least one carbon-carbon double bond. "Alkynyl" refers to an optionally substituted straight, branched, or cyclic hydrocarbon with at least one carbon-carbon triple bound. Substituted alkyl, substituted alkenyl, or substituted alkynyl refer to the respective alkyl, alkenyl or alkynyl group substituted by one or more substituents. Illustrative examples of substituents include but are not limited to alkyl, alkenyl, alkynyl, aryl, halo; trifluoromethyl; trifluoromethoxy; hydroxy; alkoxy; cycloalkoxy; heterocyclooxy; oxo (=O); alkanoyl (—C(=O)-alkyl); aryloxy; alkanoyloxy; amino; alkylamino; arylamino; aralkylamino; cycloalkylamino; heterocycloamino; disubstituted amines in which the two amino substituents are selected from alkyl, aryl, or aralkyl; alkanoylamino; aroylamino; aralkanoylamino; substituted alkanoylamino; substituted arylamino; substituted aralkanoylamino; thiol; alkylthio; arylthio; aralkylthio; cycloalkylthio; heterocyclothio; alkylthiono; arylthiono; aralkylthiono; alkylsulfonyl; arylsulfonyl; aralkylsulfonyl; sulfonamido (e.g., $SO_2NH_2$); substituted sulfonamido; nitro; cyano; carboxy; carbamyl (e.g., $CONH_2$); substituted carbamyl (e.g., —C(=O)NR'R" where R' and R" are each independently hydrogen, alkyl, aryl, aralkyl and the like); alkoxycarbonyl, aryl, guanidino, and heterocyclo such as indoyl, imidazolyl, furyl, thienyl, thiazolyl, pyrrolidyl, pyridyl, pyrimidyl and the like. Where applicable, the substituent may be further substituted such as with halogen, alkyl, alkoxy, aryl, or aralkyl and the like.

The term "aryl" refers to an optionally substituted aromatic ring having 6 to 12 carbon atoms and may include one or more heteroatoms such as N, S and O. Illustrative examples of aryl include but are not limited to biphenyl, furyl, imidazolyl, indolyl, isoquinolyl, naphthyl, oxazolyl, phenyl, pyridyl, pyrryl, quinolyl, quinoxalyl, tetrazoyl, thiazoyl, thienyl and the like. Substituted aryl refers to an aryl group substituted by, for example, one to four substituents such as substituted and unsubstituted alkyl, alkenyl, alkynyl, and aryl; halo; trifluoromethoxy; trifluoromethyl; hydroxy; alkoxy; cycloalkyloxy; heterocyclooxy; alkanoyl; alkanoyloxy; amino; alkylamino; aralkylamino; cycloalkylamino; heterocycloamino; dialkylamino; alkanoylamino; thio; alkylthio; cycloalkylthio; heterocyclothio; ureido; nitro; cyano; carboxy; carboxyalkyl; carbamyl; alkoxycarbonyl; alkylthiono; arylthiono; alkylsulfonyl; sulfonamido; aryloxy; and the like. The substituent may be further substituted, for example, by halo, hydroxy; alkyl, alkoxy; aryl, substituted aryl, substituted alkyl, substituted aralkyl, and the like.

The terms "halogen," "halo", or "halide" refer to fluorine, chlorine, bromine and iodine.

The term "subject" as used herein, refers to an animal, preferably a mammal, or, most preferably, a human, that is the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

In one aspect, the present invention provides compounds of the formula

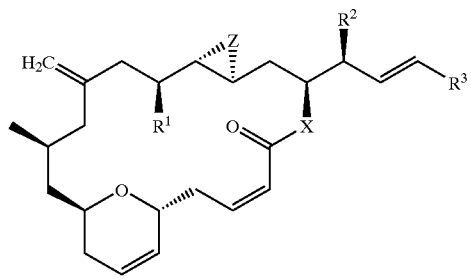

wherein:

X is O or NR, wherein R is H, $C_1$–$C_{10}$ alkyl, $C_2$–$C_{10}$ alkenyl, $C_2$–$C_{10}$ alkynyl, aryl, alkylaryl, alkenylaryl, or alkynylaryl;

Z is O, $CH_2$, or a bond;

$R^1$ is hydrogen, hydroxyl, $C_1$–$C_{10}$ alkoxy, aryloxy, or alkylaryloxy;

$R^2$ is hydrogen, hydroxyl, $C_1$–$C_{10}$ alkoxy, aryloxy, or alkylaryloxy; and $R^3$ is cyclohexyl, 3-cyclohexenyl, phenyl, or a group of the formula

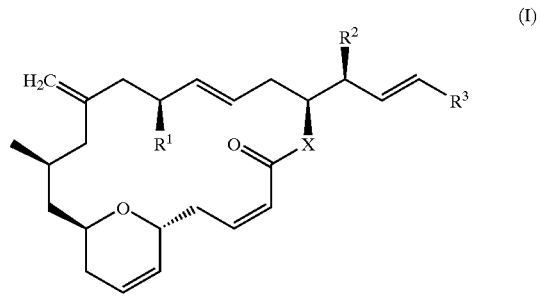

or

In one embodiment of the invention, the laulimalide compounds of formula (I) are provided

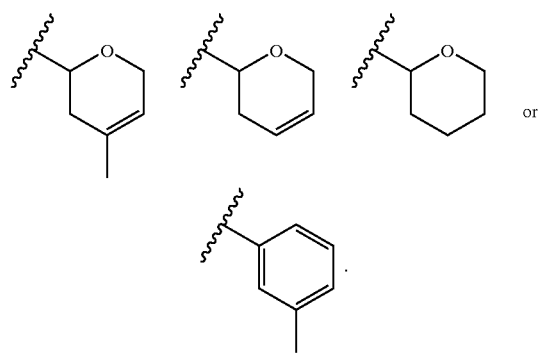

(I)

wherein:

X is O or NR, wherein R is H, $C_1$–$C_{10}$ alkyl, $C_2$–$C_{10}$ alkenyl, $C_2$–$C_{10}$ alkynyl, aryl, arylalkyl, arylalkenyl, or arylalkynyl;

$R^1$ is H, OH, $C_1$–$C_{10}$ alkoxy, aryloxy, or alkylaryloxy;

$R^2$ is H, OH, $C_1$–$C_{10}$ alkoxy, aryloxy, or alkylaryloxy; and $R^3$ is cyclohexyl, 3-cyclohexenyl, phenyl, or a group of the formula

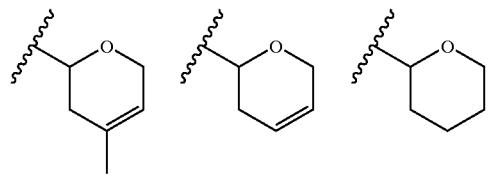 or

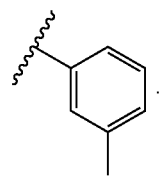.

In another embodiment of the invention, compounds of formula (I) are provided wherein X=O or NR, wherein R is H, $C_1$–$C_5$ alkyl, phenyl, or benzyl;

$R^1$ is OH, or $C_1$–$C_5$ alkoxy, $R^2$ is H, OH, or $C_1$–$C_5$ alkoxy; and $R^3$ is cyclohexyl, 3-cyclohexenyl, phenyl, or a group of the formula

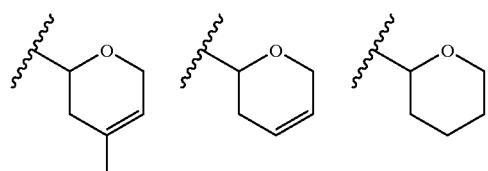 or

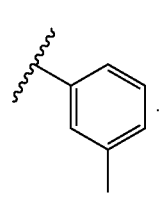.

In another embodiment of the invention, compounds of formula (I) are provided wherein X=O or NH;

$R^1$ is OH, or $C_1$–$C_5$ alkoxy;

$R^2$ is H, OH, or $C_1$–$C_5$ alkoxy; and $R^3$ is a group of the formula

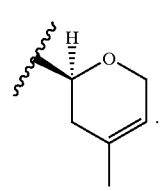.

In another embodiment of the invention, the compounds of formula (I) having the formulas

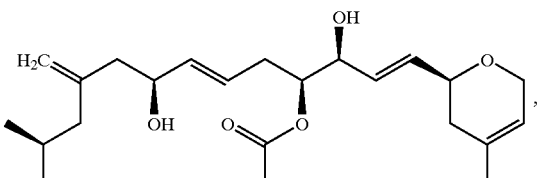,

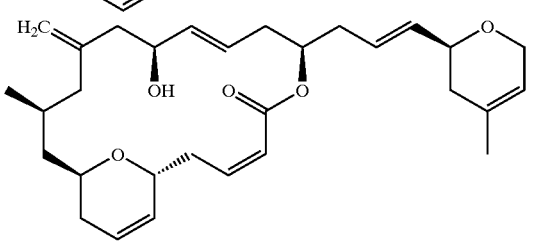,

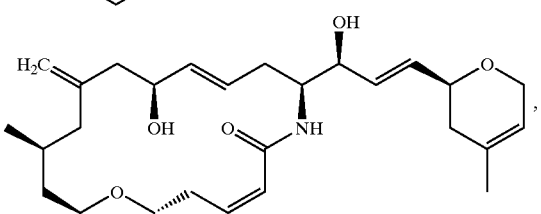,

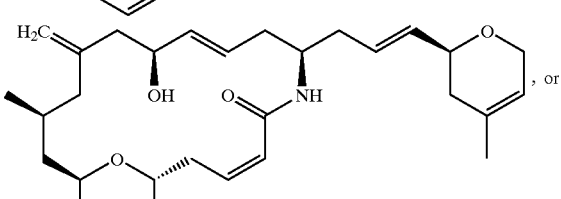, or

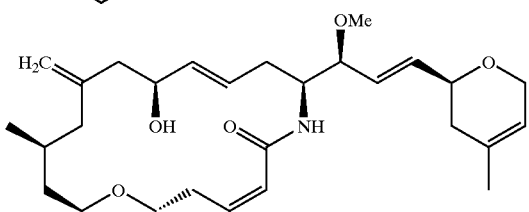

are provided.

In another embodiment of the invention, compounds of formulas (II) are provided

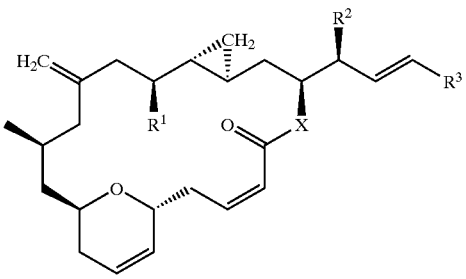

(II)

wherein:
X is O or NR, wherein R is H, $C_1$–$C_{10}$ alkyl, $C_2$–$C_{10}$ alkenyl, $C_2$–$C_{10}$ alkynyl, aryl, arylalkyl, arylalkenyl, or arylalkynyl;
$R^1$ is H, OH, $C_1$–$C_{10}$ alkoxy, aryloxy, or alkylaryloxy;
$R_2$ is H, OH, $C_1$–$C_{10}$ alkoxy, aryloxy, or alkylaryloxy; and
$R^3$ is cyclohexyl, 3-cyclohexenyl, phenyl, or a group of the formula

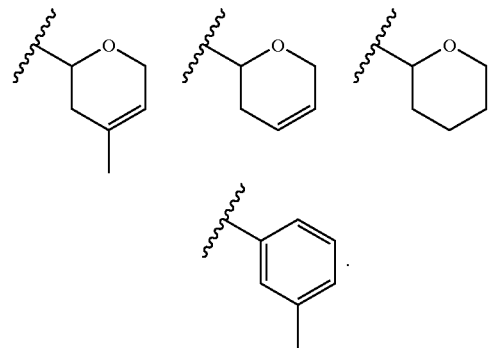

or

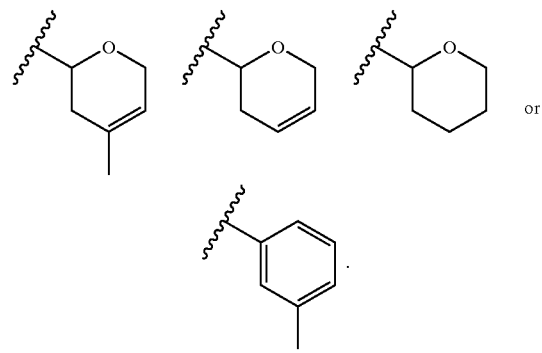

.

In another embodiment of the invention, compounds of formula (II) are provided wherein
X=O or NR, wherein R is H, $C_1$–$C_5$ alkyl, phenyl, or benzyl;
$R^1$ is OH, or $C_1$–$C_5$ alkoxy;
$R^2$ is H, OH, or $C_1$–$C_5$ alkoxy; and
$R^3$ is cyclohexyl, 3-cyclohexenyl, phenyl, or a group of the formula In another embodiment of the invention, compounds of formula (II) are provided wherein
X=O or NH;
$R^1$ is OH, or $C_1$–$C_5$ alkoxy;
$R^2$ is H, OH, or $C_1$–$C_5$ alkoxy; and
$R^3$ is a group of the formula

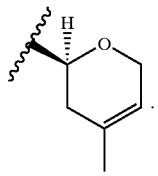

.

In another embodiment of the invention, the compounds of formula (II) having the formulas

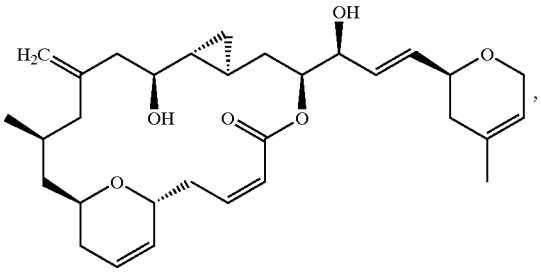

,

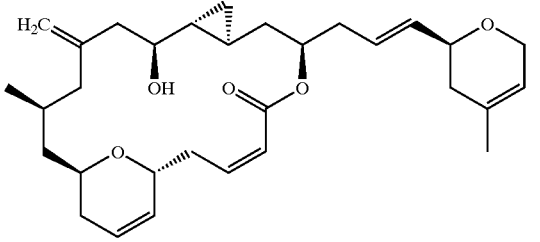

,

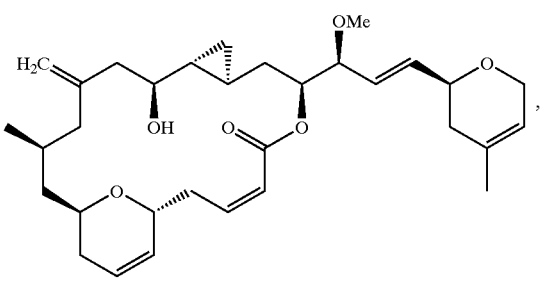

,

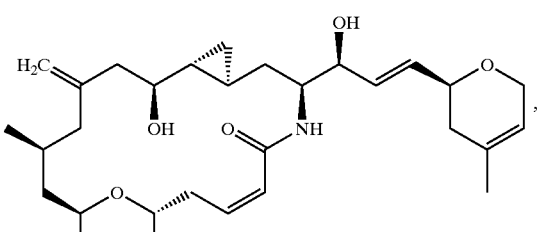

,

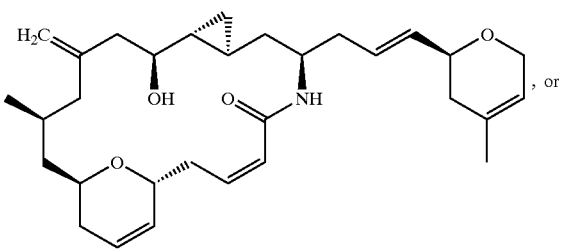

, or

-continued

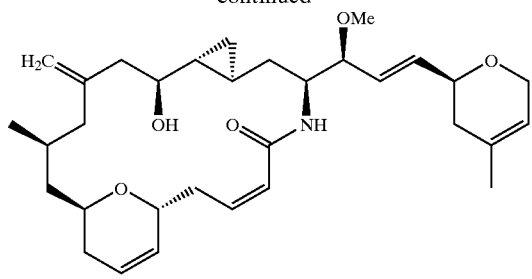

are provided.

In another embodiment of the invention, compounds of formulas (III) are provided (III)

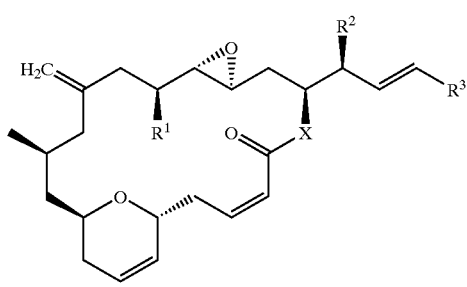

wherein:

X is O or NR, wherein R is H, $C_1$–$C_{10}$ alkyl, $C_2$–$C_{10}$ alkenyl, $C_2$–$C_{10}$alkynyl, aryl, arylalkyl, arylalkenyl, or arylalkynyl;

$R^2$ is H, $C_1$–$C_{10}$ alkoxy, aryloxy, or alkylaryloxy; and $R^3$ is cyclohexyl, 3-cyclohexenyl, phenyl, or a group of the formula

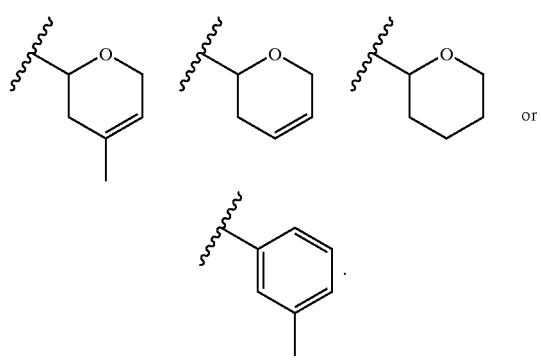

In another embodiment of the invention, compounds of formula (III) are provided wherein X=O or NR, wherein R is H, $C_1$–$C_5$ alkyl, phenyl, or benzyl;

$R^2$ is H or $C_1$–$C_5$ alkoxy; and $R^3$ is cyclohexyl, 3-cyclohexenyl, phenyl, or a group of the formula

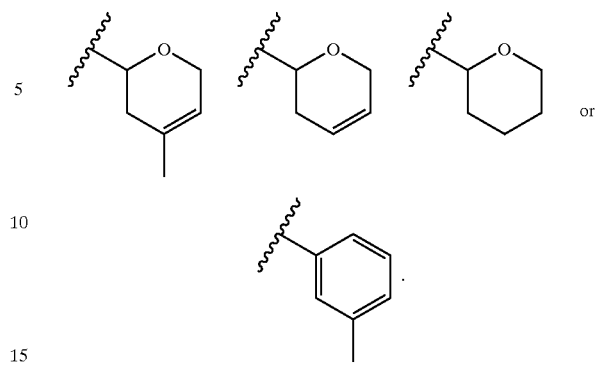

In another embodiment of the invention, compounds of formula (III) are provided wherein X=O or NH;

$R^2$ is H or $C_1$–$C_5$ alkoxy; and $R^3$ is a group of the formula

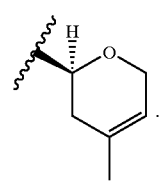

In another embodiment of the invention, the compounds of formula (III) having the formulas

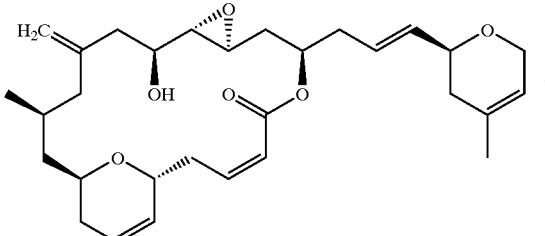

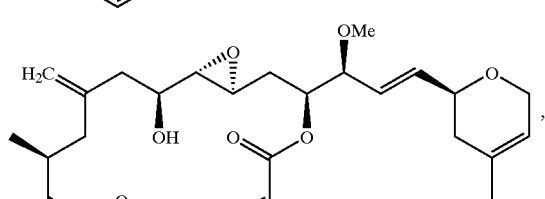

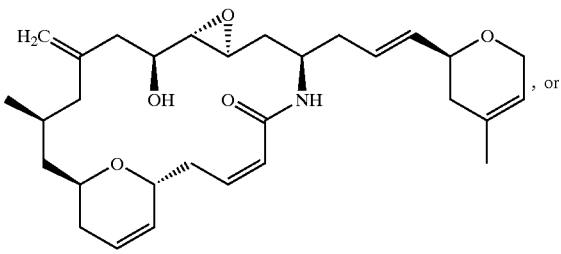

-continued

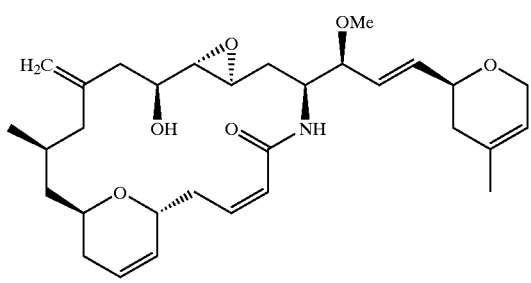

are provided.

The compounds of the present invention possess paclitaxel-like microtubule stabilizing activity and are potent inhibitors of cell proliferation. Based on initial studies on paclitaxel-resistant cell line SKVLB-1, these compounds are expected to be active against paclitaxel-resistant tumors since they appear to be poor substrates for P-glycoprotein mediated transport. In addition to being anti-cancer agents, the compounds of the present invention may be used to treat other diseases that are characterized by cellular hyperproliferation such as many inflammatory disorders, for example psoriasis, eczema, dermatitis, multiple sclerosis, and rheumatoid arthritis, and restenosis. The compounds of the invention have further utility to kill cells, ameliorate the detrimental effects of cell growth, and generally to substitute for any other cytotoxic agent in any application thereof.

The compounds of the present invention are expected to be more resistant to degradation than is laulimalide. Isolaulimalide (which is a less potent stabilizer of microtubule polymerization than laulimalide) is a degradation product of laulimalide, formed by attack of the 20-OH on the reactive 16,17-epoxide. Neolaulimalide may also be a degradation product resulting from translactonization from $O_{19}$ to $O_{20}$. Alterations to the laulimalide structure that would block such degradative processes are expected to increase the effectiveness of laulimalide as an antimitotic agent.

Thus, in one embodiment of the invention, the 16,17-epoxide is replaced with an alkene to form 16,17-desoxylaulimalide. It is likely that this change would increase the therapeutic index as well as increase the stability of laulimalide, based on similar findings with epothilone B and its desoxy-analog, epothilone D.

In another embodiment of the invention, the 16,17-epoxide is replaced with a cyclopropane in order to stabilize laulimalide against rearrangement to isolaulimalide.

In another embodiment of the invention, the reactive 20-OH group is either removed or blocked as a 20-O-alkyl ether derivative. Removal of the nucleophilic 20-OH group will prevent rearrangement of laulimalide to isolaulimalide.

In another embodiment of the invention, the lactone group is replaced with a lactam to give laulimalide lactams. Laulimalide lactams are expected to be resistant towards formation of neolaulimalides.

In another embodiment of the invention, the modifications described above are combined to produce highly stabilized laulimalide compounds. Thus, for example, the lactam analogs of 16,17-desoxylaulimalide, cyclopropyl laulimalides, 20-deoxylaulimalides, and 20-O-alkyl ether laulimalides will be stabilized against degradation to both isolaulimalides and neolaulimalides.

In another aspect of the invention, methods for the conversion of laulimalide into more stable derivatives are provided. Laulimalide itself is available either through total synthesis as described above or through isolation from natural sources, as described in Quinoa et al., "Fijianolides, polyketide heterocycles from a marine sponge," *J. Org. Chem.* 1988, 53: 3642–3; Corley et al., "Laulimalides. New potent cytotoxic macrolides from a marine sponge and a nudibranch predator," *J. Org. Chem.* 1988, 53: 3644–6; and Mooberry & Davidson, "Laulimalide compounds as microtubule stabilizing agents," PCT publication WO 01/54689; each of which is incorporated herein by reference in its entirety.

In one embodiment, laulimalide is deoxygenated using titanocene dichloride ($TiCp_2Cl_2$) and magnesium to provide 16,17-desoxylaulimalide. Similar reagents useful for this transformation include that of Sharpless, tungsten hexachloride ($WCl_6$) and n-butyllithium, and that of Yadav et al., titanocene dichloride with zinc and zinc chloride. In one form of this embodiment, laulimalide is directly treated with the deoxygenation reagent to provide 16,17-desoxylaulimalide. In a preferred form of the embodiment, laulimalide (1) is first reacted with a silylating agent, for example tert-butyldimethylsilyl chloride or triflate, in the presence of a mild base such as imidazole or 2,6-lutidine, so as to protect the 15- and 20-hydroxyl groups as their silyl ethers (4) as illustrated in Scheme 1. Compound (4) is then reacted with the deoxygenating reagent to produce the protected compound (5). Subsequent desilylation with HF would provide 16,17-desoxylaulimalide (6).

SCHEME 1

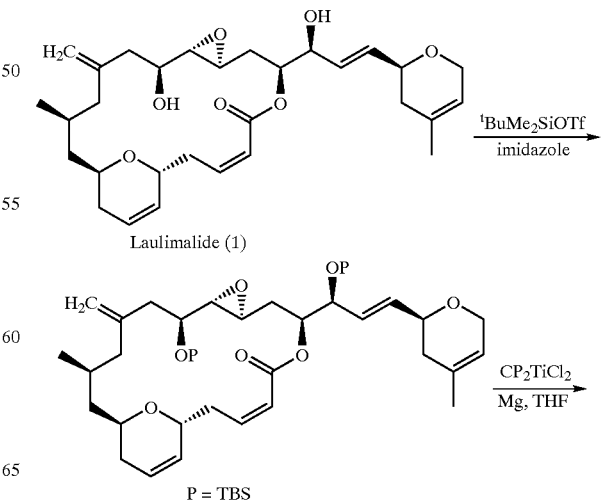

-continued

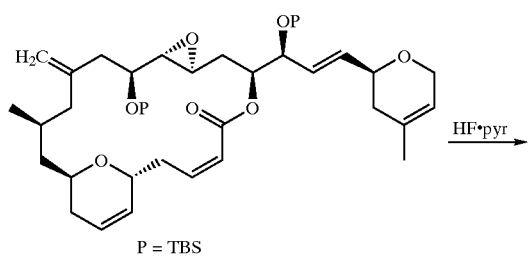

P = TBS

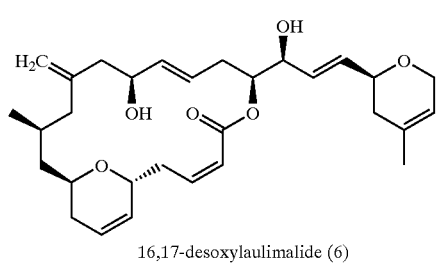

16,17-desoxylaulimalide (6)

In another embodiment, methods for conversion of 16,17-desoxylaulimalide into the cyclopropane derivative 16,17-desoxy-16,17-methylenelaulimalide (7) are provided.

Cyclopropanation is affected using the Simmons-Smith procedure as illustrated in Scheme 2. This reagent ($CH_2I_2$ with a Zn/Cu couple) and later improvements thereof, for example $Et_2Zn$ and $CH_2I_2$, rely upon the directing effect of an adjacent alcohol to deliver a $CH_2$ equivalent to the olefin of an allylic alcohol. There are two such allylic alcohols present in 16,17-deoxylaulimalide (positions 15 and 20), leading to possible formation of two monocyclopropanes and a bis(cyclopropane), yet the 16,17-alkene is known to be more reactive.

SCHEME 2

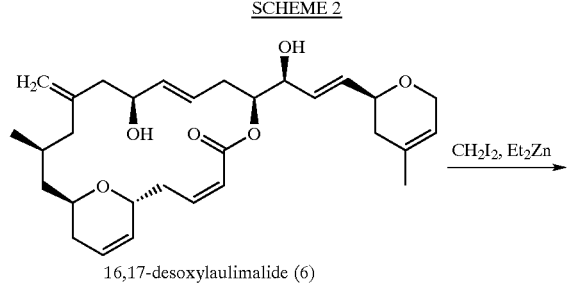

16,17-desoxylaulimalide (6)

-continued

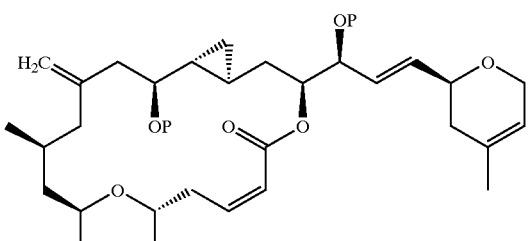

16,17-desoxy-16,17-methylenelaulimalide (7)

In other embodiments of the present invention, methods for preparation of laulimalides modified at the 20-position are provided. In general, these methods involve initial conversion of a laulimalide compound into a 15,20-diester derivative (8) as illustrated in Scheme 3.

SCHEME 3

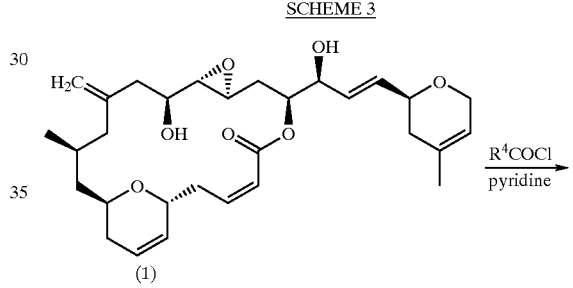

(1)

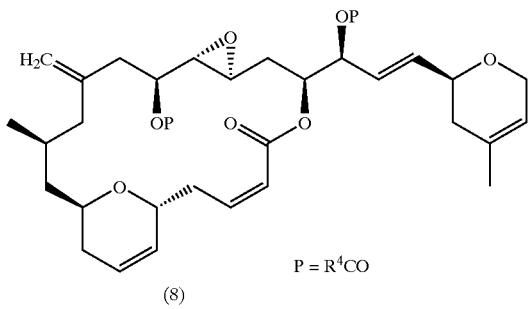

P = $R^4$CO (8)

In one embodiment, deoxygenation is performed by treatment of a 20-O-ester with a metal catalyst and a hydride source as illustrated in Scheme 4. Subsequent deprotection of the 15-OH provides 20-deoxylaulimalide (10). Methods for deoxygenating the 20-OH include but are not limited to reaction of a 20-O-cinnamate ester (8, $R^4$=PhCH=CH—) with triethylsilane and $(Ph_3P)_3RhCl$, and treatment of the 20-O-acetate ester (8, $R^4$=Me) with formic acid and a palladium catalyst. In another embodiment, the epoxide of the 20-deoxylaulimalide is deoxygenated according to the methods described above to provide 20-deoxy-16,17-desoxylaulimalide (12) after deprotection.

SCHEME 4

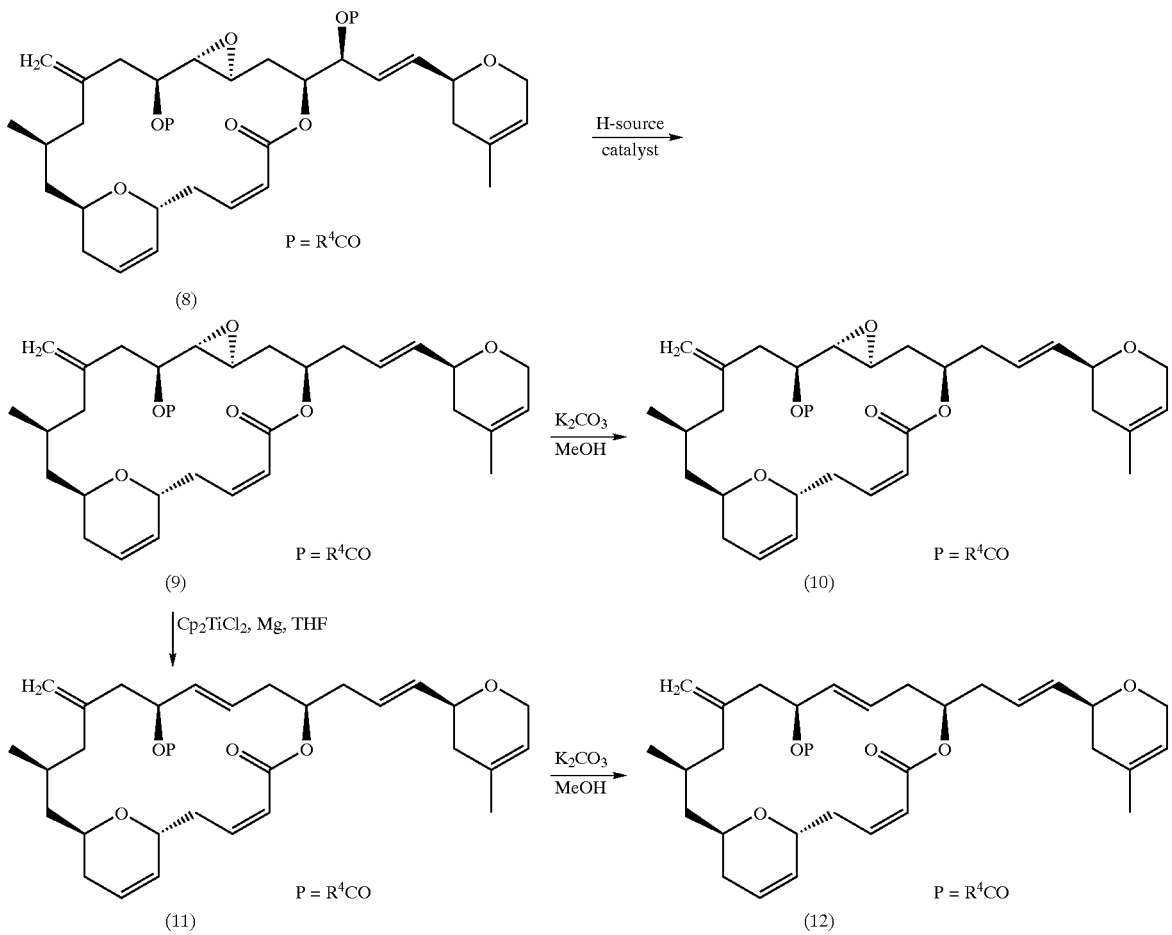

In another embodiment of the invention, methods for the preparation of 20-O-alkyl ethers (13) of laulimalide are provided. A laulimalide 15,20-dicarbonate (8, $R^4$=$OR^5$) is treated with a palladium catalyst, for example tetrakis(triphenylphosphine)palladium, to effect nucleophilic replacement of the 20-oxygen by the alkoxy group $OR^5$ as illustrated in Scheme 5. The alkyl group $R^5$ of the ether can be varied by changing the carbonate. In a preferred embodiment, $R^5$ is methyl. In another embodiment of the invention, the 16,17-epoxide is deoxygenated, and the resulting 15-carbonate either cleaved to yield (14) or resubmitted to the palladium reaction to generate a 15,20-bisether (15). In another embodiment, compound (14) is converted into a new 15-O-carbonate and then subjected to the palladium reaction so as to provide a 15,20-bisether (15) wherein the $R^5$ groups at 15 and 20 are different.

SCHEME 5

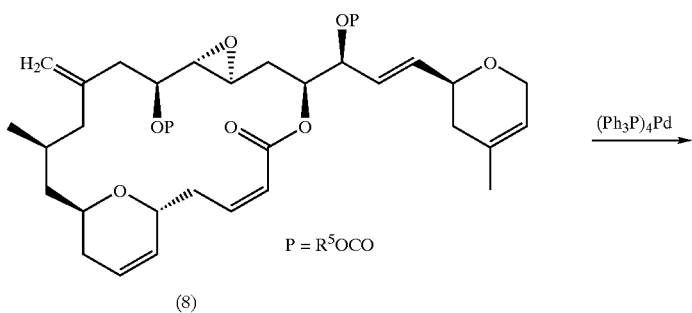

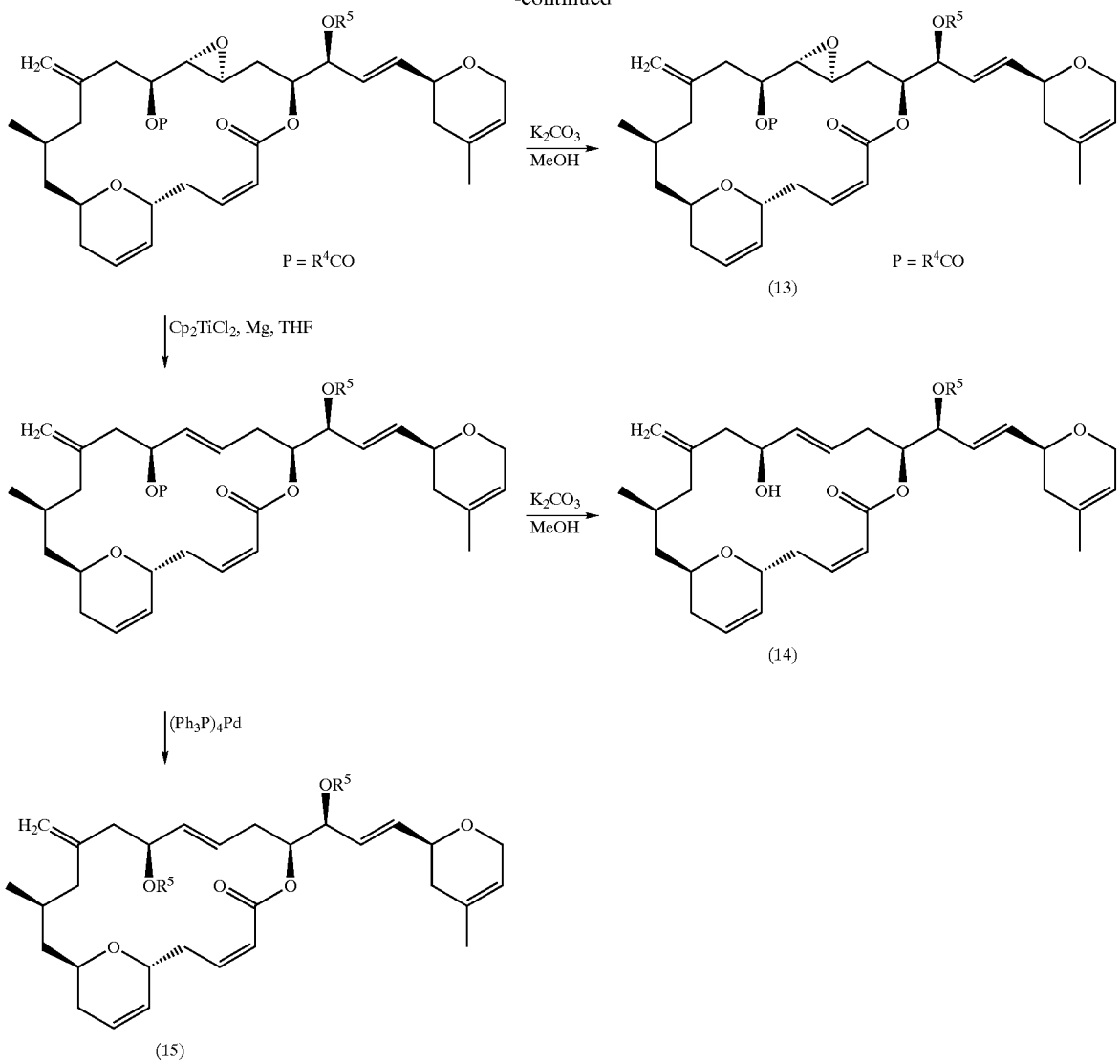

In another aspect of the invention, laulimalide analogs are made by de novo synthesis. Scheme 6 illustrates the disconnection of laulimalide into two fragments, A and B, which are used to prepare laulimalide analogs by total synthesis according to the methods described in Paterson et al., "Total synthesis of the microtubule-stabilizing agent (−)-laulimalide," *Org. Letts*/2001, 3: 3149–3152.

SCHEME 6

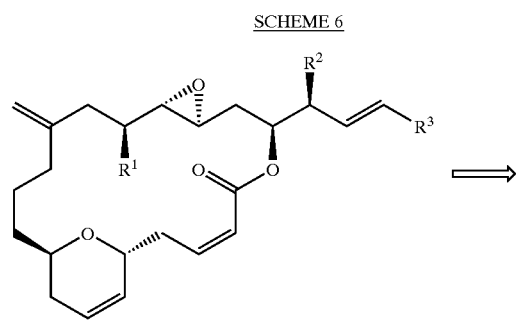

-continued

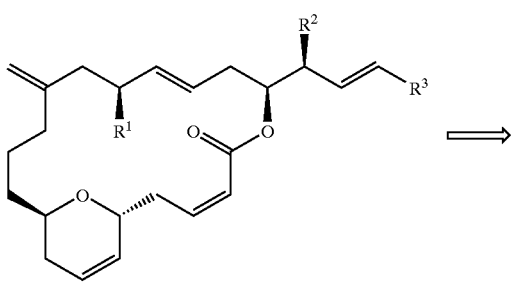

-continued

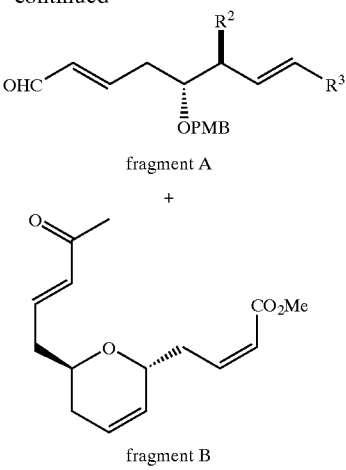

fragment A

+ fragment B

In one embodiment of the invention, 20-deoxylaulimalides are prepared by use of the A fragment wherein $R^2$=H. Scheme 7 illustrates a method for preparation of this A fragment.

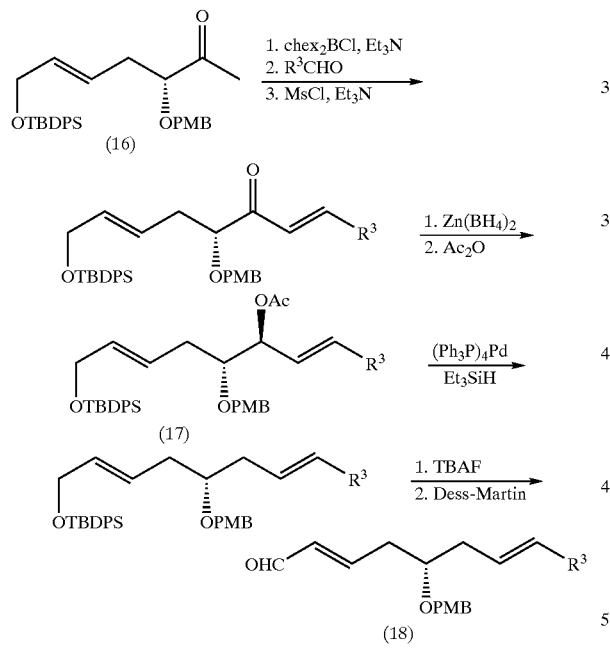

Aldol condensation of compound (16), prepared as described in Paterson et al., with aldehyde $R^3$CHO followed by dehydration of the aldol adduct using methanesulfonyl chloride and triethylamine introduces the $R^3$ group. For example, condensation with benzaldehyde will yield the fragment wherein $R^3$ is a phenyl group, condensation with cyclohexanecarboxaldehyde will yield the fragment wherein $R^3$ is a cyclohexyl group, condensation with 3-pyridinecarboxaldehyde will yield the fragment wherein $R^3$ is a 3-pyridyl group, and condensation with thiazole-4-carboxaldehyde will yield the fragment wherein $R^3$ is a 4-thiazolyl group. Substituted aldehydes are used similarly to provide fragments where $R^3$ is e.g., a substituted phenyl, cyclohexyl, cyclohexenyl, pyridyl, or thiazolyl group. The resulting ketone is selectively reduced using zinc borohydride, and the alcohol so produced is acetylated using acetic anhydride and pyridine to provide compound (17). The allylic acetate is reduced using a palladium catalyst such as tetrakis-(triphenylphosphine)palladium and a hydride donor, such as triethylsilane, formic acid, or the like. Finally, the terminal aldehyde is installed by removal of the tert-butyldiphenylsilyl protecting group and oxidation of the resulting alcohol, for example using the Dess-martin periodinane, Swern oxidation (oxalyl chloride, DMSO, triethylamine), or the like, to produce fragment A wherein $R^2$=H.

In one embodiment of the invention, 20-O-alkyl ether laulimalides are prepared by use of the A fragment wherein $R^2$=$OR^5$. Scheme 8 illustrates a method for preparation of this A fragment.

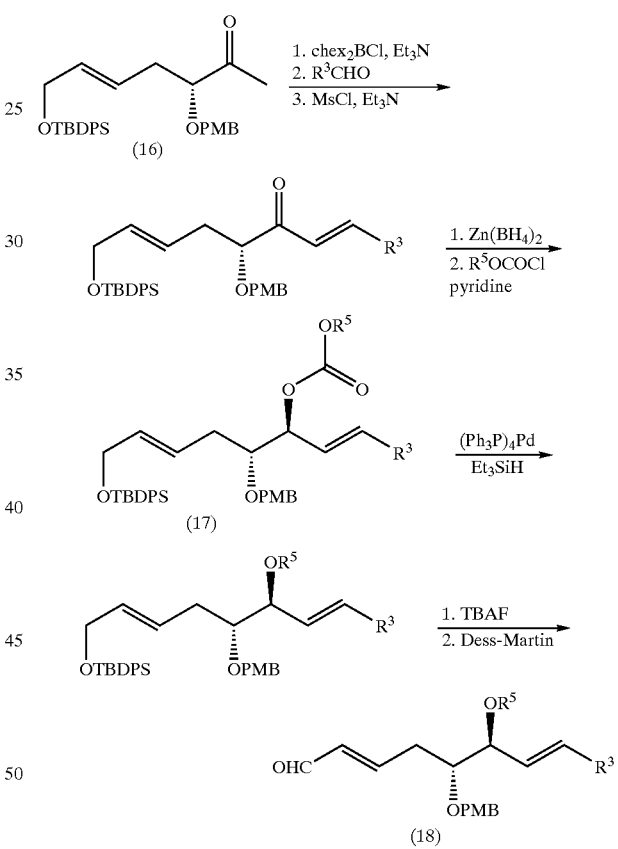

The $R^3$ group is introduced, and the ketone reduced as discussed above. The alcohol is reacted with an alkyl chloroformate and pyridine to produce the carbonate (17), which is treated with a palladium catalyst such as tetrakis (triphenylphosphine)palladium to produce the ether. Elaboration of the terminal aldehyde as discussed above provides the A fragment wherein $R^2$=$OR^5$.

Scheme 9 illustrates the use of the above-described fragments in the preparation of compounds of the invention.

SCHEME 9

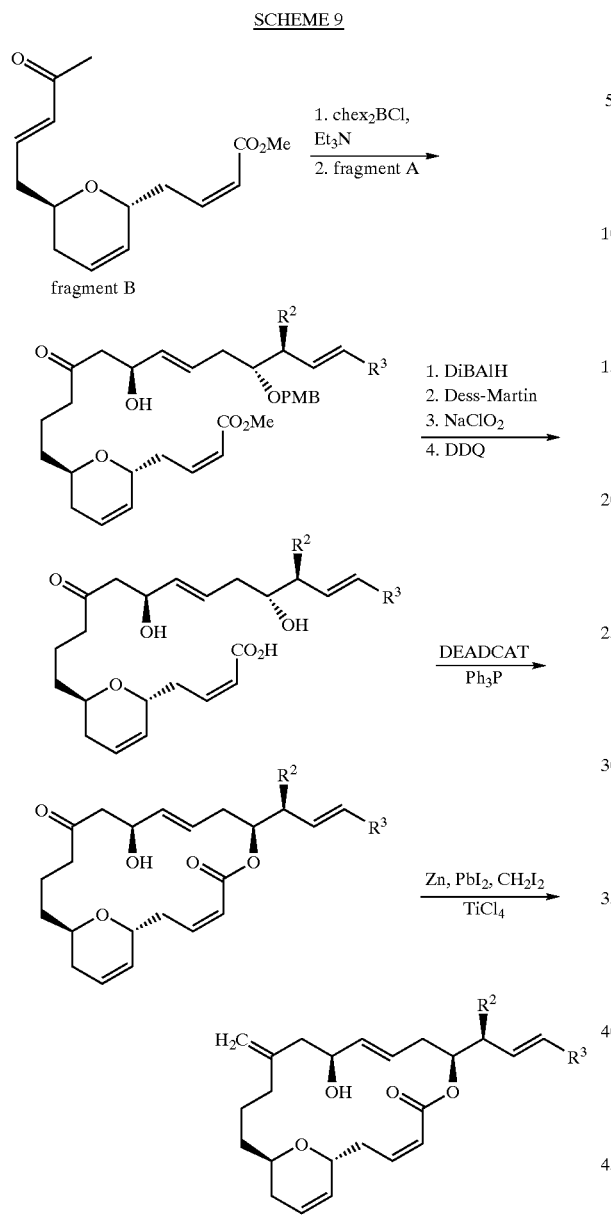

Aldol condensation of the A and B fragments using the boron enolate is followed by conversion of the methyl ester to the acid via a three-step sequence of reduction to the alcohol (diusobutylaluminum hydride at −78° C.), oxidation of the alcohol to an aldehyde (Dess-Martin periodinane), and oxidation of the aldehyde to the carboxylic acid (NaClO$_2$ in the presence of disodium phosphate, 2-methyl-2-butene, and tert-butanol). The PMB protecting group is removed by treatment with dichlorodicyanoquinone (DDQ) in buffered dichloromethane. The lactone is formed by Mitsunobu inversion using diethyl azodicarboxylate (DEADCAT) and triphenylphosphine. The 13-ketone is then converted into the 13-methylidene group using the Takai reagent (zinc, lead iodide, duiodomethane, and titanium tetrachloride in THF).

In another embodiment of the invention, laulimalide lactams are prepared through total synthesis according to the retrosynthetic analysis shown in Scheme 10.

SCHEME 10

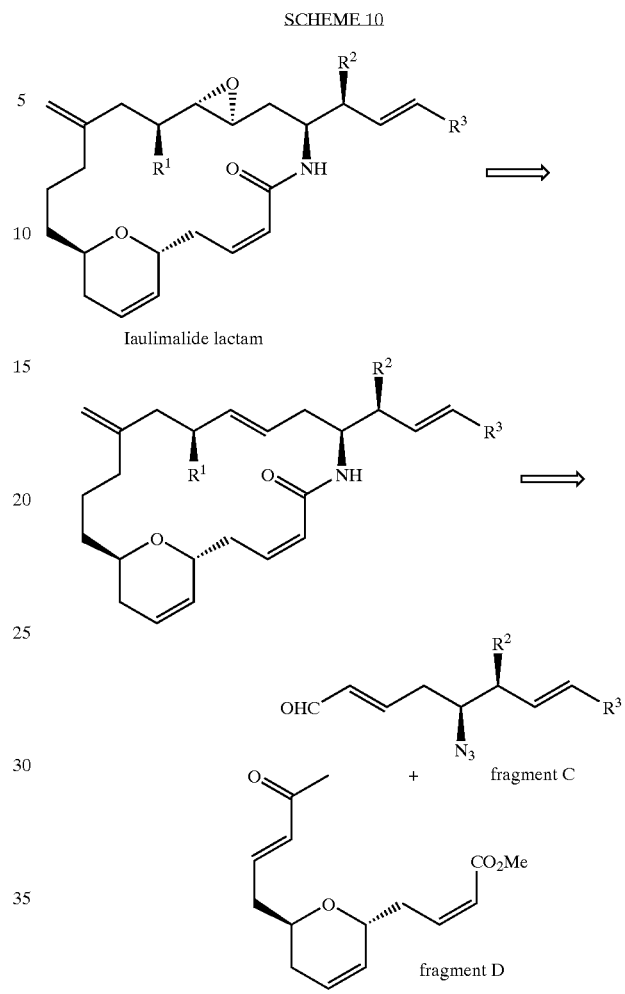

The laulimalide lactam is prepared from two main fragments of the molecule, an azide-containing "fragment C" and a ketone-containing "fragment D." In one embodiment of the invention, fragment C wherein $R^2$ is tert-butyldimethylsilyloxy (OTBS) is prepared starting from compound (16) described above as illustrated in Scheme 11.

SCHEME 11

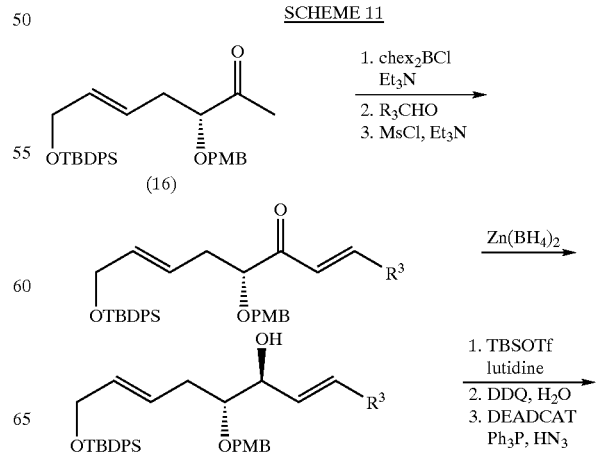

-continued

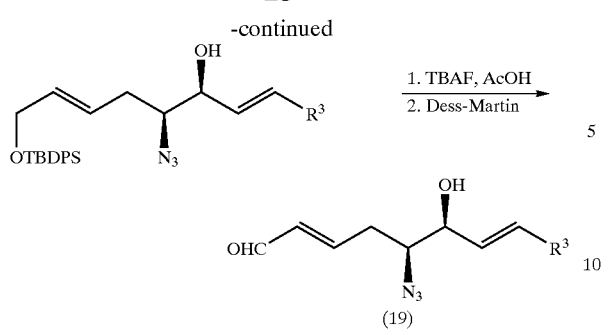

(19)

Aldol condensation of (16) with an aldehyde via the boron enolate adds the R³ group as described above. For example, condensation with benzaldehyde will yield the fragment wherein R³ is a phenyl group, condensation with cyclohexanecarboxaldehyde will yield the fragment wherein R³ is a cyclohexyl group, condensation with 3-pyridinecarboxaldehyde will yield the fragment wherein R³ is a 3-pyridyl group, and condensation with thiazole-4-carboxaldehyde will yield the fragment wherein R³ is a 4-thiazolyl group. Substituted aldehydes are used similarly to provide fragments where R³ is e.g., a substituted phenyl, cyclohexyl, cyclohexenyl, pyridyl, or thiazolyl group. The intermediate aldol adduct is dehydrated using methanesulfonyl chloride and an amine base. The ketone group is reduced diastereoselectively using zinc borohydride at −40° C., and the resulting alcohol is protected as its tert-butyldimethylsilyl ether. The PMB ether is selectively removed by treatment with dichlorodicyanoquinone (DDQ) in the presence of water, and the resulting alcohol is displaced with azide with stereochemical inversion by treatment with HN₃ in the presence of diethyl azodicarboxylate (DEADCAT) and triphenylphosphine. Finally, the tert-butyldiphenylsilyl group is selectively removed using buffered tetrabutylammonium fluoride, and the resulting alcohol is oxidized to the aldehyde, for example using the Dess-Martin periodinane or Swern conditions (oxalyl chloride, DMSO, triethylamine), to provide (19), fragment C wherein R² is OTBS.

In another embodiment, fragment C wherein R²=alkoxy is prepared as illustrated in Scheme 12.

SCHEME 12

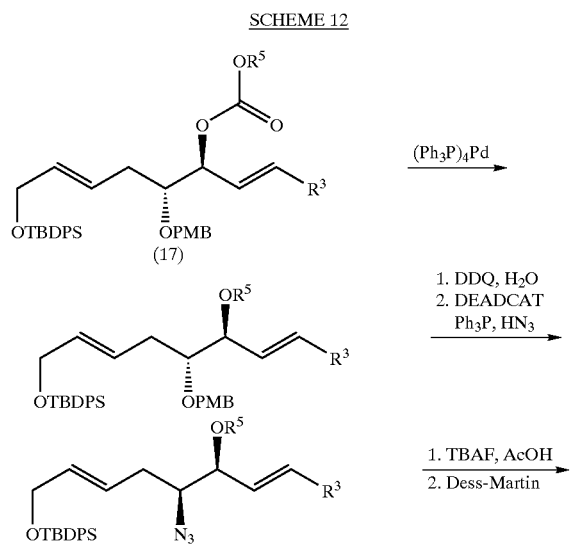

-continued

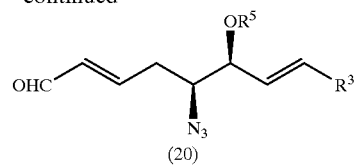

(20)

The carbonate intermediate (17) from Scheme 8 is treated with a palladium catalyst such as tetrakis(triphenylphosphine)palladium to form the ether. The PMB protecting group is removed using DDQ, and the alcohol is converted to the azide with inversion of configuration using DEADCAT, triphenylphosphine, and HN₃. The terminal aldehyde is installed as described above, yielding (20), fragment C wherein R²=alkoxy.

In another embodiment, fragment C wherein R²=H is prepared, that is used to prepare 20-deoxy analogs of laulimalide lactams. As illustrated in Scheme 13, these fragments are prepared using a variation of the method of Scheme 11 wherein the alcohol is first acylated, for example using acetic anhydride and a base, then reduced using a palladium catalyst and a hydride source such as triethylsilane or formic acid.

SCHEME 13

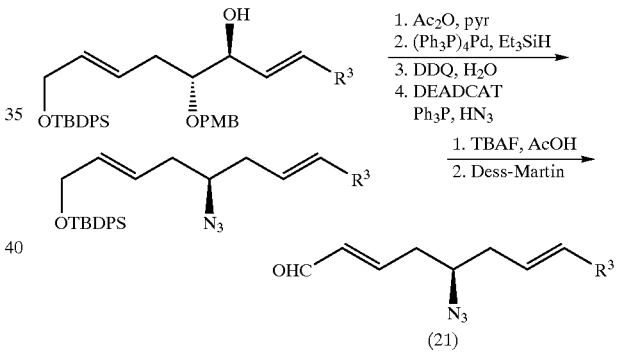

(21)

The azide is installed as described above, followed by introduction of the terminal aldehyde to produce (21), fragment C wherein R²=H.

The D fragment is prepared as illustrated in Scheme 14.

SCHEME 14

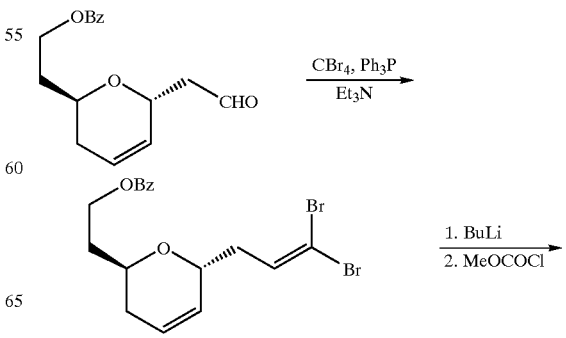

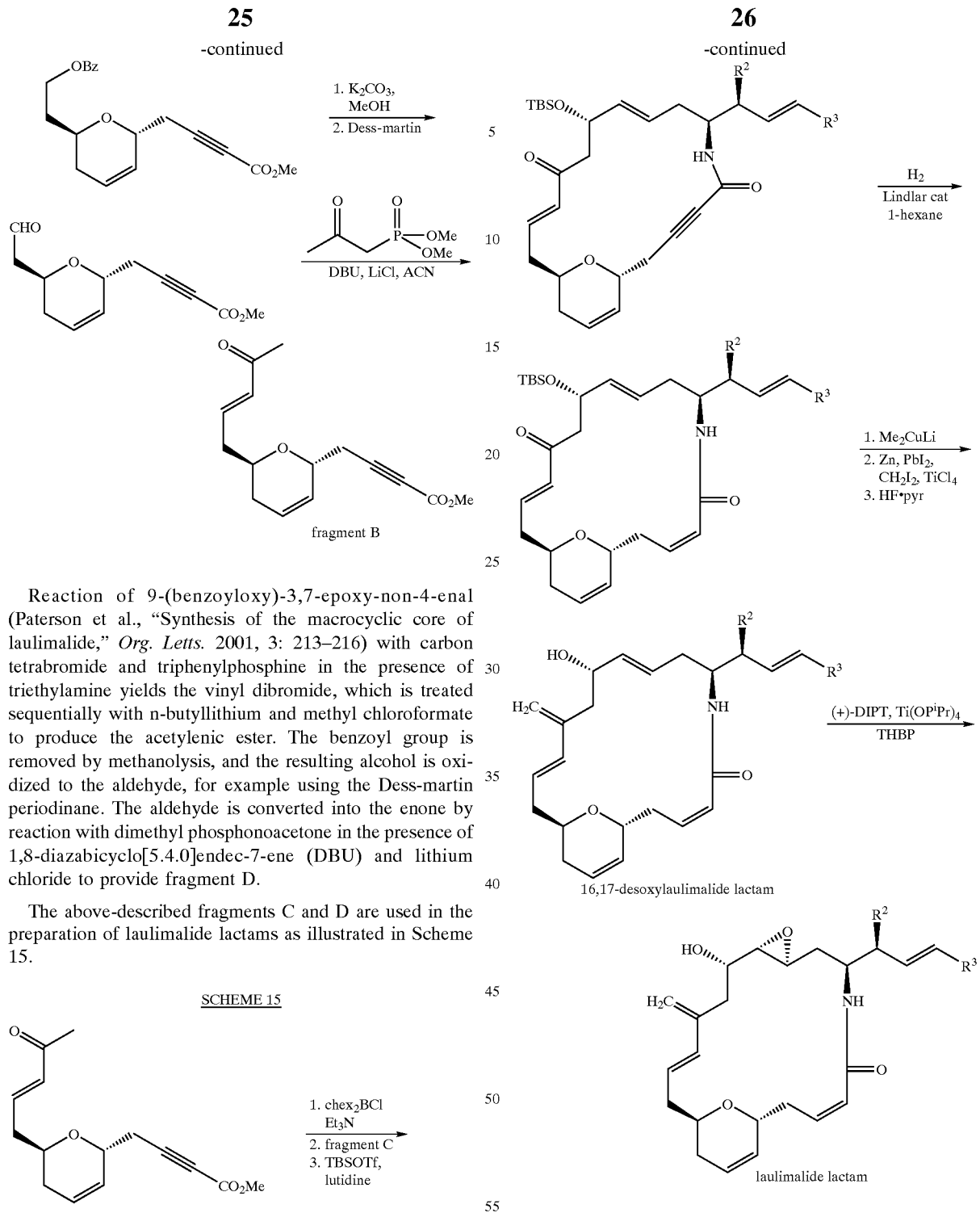

Reaction of 9-(benzoyloxy)-3,7-epoxy-non-4-enal (Paterson et al., "Synthesis of the macrocyclic core of laulimalide," *Org. Letts.* 2001, 3: 213–216) with carbon tetrabromide and triphenylphosphine in the presence of triethylamine yields the vinyl dibromide, which is treated sequentially with n-butyllithium and methyl chloroformate to produce the acetylenic ester. The benzoyl group is removed by methanolysis, and the resulting alcohol is oxidized to the aldehyde, for example using the Dess-martin periodinane. The aldehyde is converted into the enone by reaction with dimethyl phosphonoacetone in the presence of 1,8-diazabicyclo[5.4.0]endec-7-ene (DBU) and lithium chloride to provide fragment D.

The above-described fragments C and D are used in the preparation of laulimalide lactams as illustrated in Scheme 15.

SCHEME 15

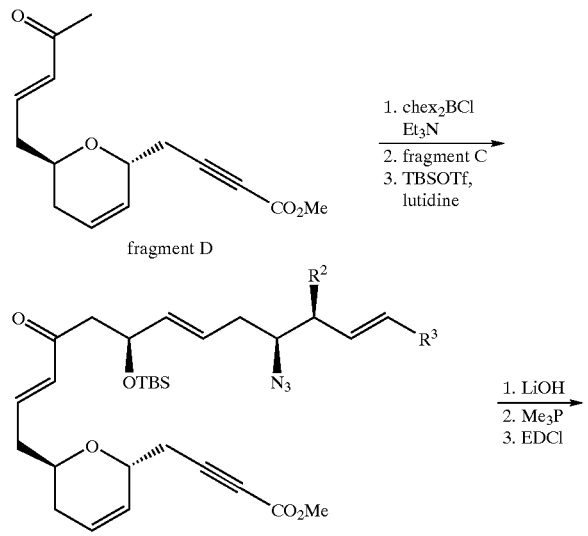

Fragment C is coupled to fragment D using a boron-mediated aldol condensation, and the OH group of the aldol adduct is protected as its silyl ether, for example using tert-butyldimethylsilyl triflate and a mild base such as 2,6-lutidine. The ester is saponified using lithium hydroxide in water/tetrahydrofuran to provide the acid. The azide is reduced using a phosphine such as trimethylphosphine in the presence of water, and the lactam is then formed by condensation with a carbodiimide reagent such as 1-[3-(dimethylamino)propyl]-3-ethylcarbodiimide hydrochloride (EDCI). The alkyne is partially hydrogenated to form the cis-alkene using Lindlar's catalyst in the presence of 1-hexene. The 11-methyl group is installed by lithium dimethylcuprate addition to the enone, and the 13-ketone is converted to the 13-methylidene group using the Takai reagent, diuodomethane in the presence of zinc metal, lead iodide, and titanium tetrachloride. Removal of the silyl ether protecting groups using HF·pyridine yields the 16,17-desoxylaulimalide lactam. In another embodiment of the invention, the 16,17-desoxylaulimalide lactam is converted into the laulimalide lactam by selective epoxidation using Sharpless conditions (diisopropyltartrate, titanium tetraisopropoxide, and tert-butylhydroperoxide). Use of the (+)-isomer of diisopropyltartrate provides the naturally-occurring diastereomer of the epoxide.

In another embodiment of the invention, laulimalide lactams are prepared using modifications of the method described in Ghosh et al., 2001, "Total synthesis of microtubule-stabilizing agent (−)-laulimalide," *J. Org. Chem.* 66: 8973–8982 as illustrated in Scheme 16.

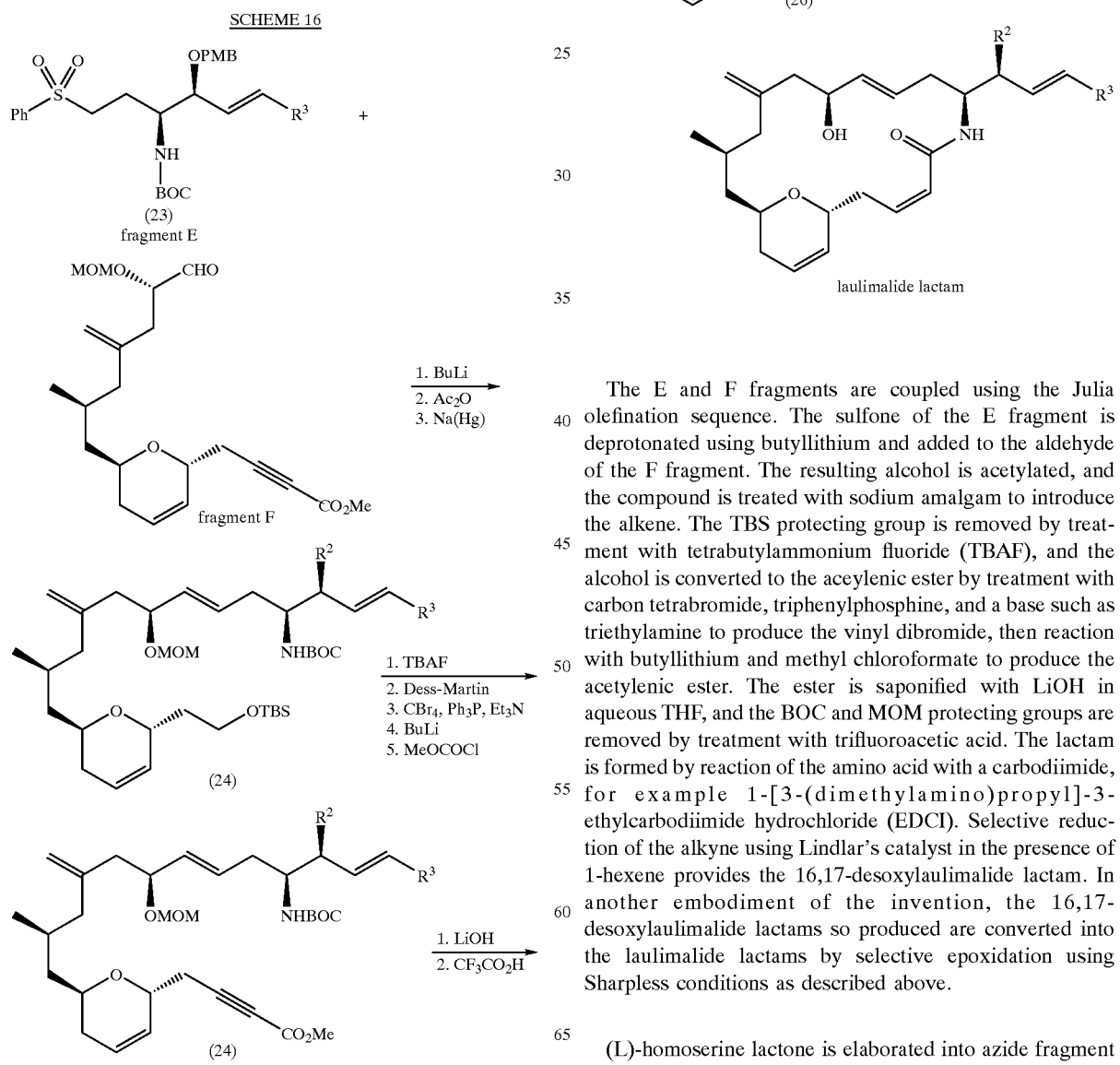

The E and F fragments are coupled using the Julia olefination sequence. The sulfone of the E fragment is deprotonated using butyllithium and added to the aldehyde of the F fragment. The resulting alcohol is acetylated, and the compound is treated with sodium amalgam to introduce the alkene. The TBS protecting group is removed by treatment with tetrabutylammonium fluoride (TBAF), and the alcohol is converted to the aceylenic ester by treatment with carbon tetrabromide, triphenylphosphine, and a base such as triethylamine to produce the vinyl dibromide, then reaction with butyllithium and methyl chloroformate to produce the acetylenic ester. The ester is saponified with LiOH in aqueous THF, and the BOC and MOM protecting groups are removed by treatment with trifluoroacetic acid. The lactam is formed by reaction of the amino acid with a carbodiimide, for example 1-[3-(dimethylamino)propyl]-3-ethylcarbodiimide hydrochloride (EDCI). Selective reduction of the alkyne using Lindlar's catalyst in the presence of 1-hexene provides the 16,17-desoxylaulimalide lactam. In another embodiment of the invention, the 16,17-desoxylaulimalide lactams so produced are converted into the laulimalide lactams by selective epoxidation using Sharpless conditions as described above.

(L)-homoserine lactone is elaborated into azide fragment E as illustrated in Scheme 17.

SCHEME 17

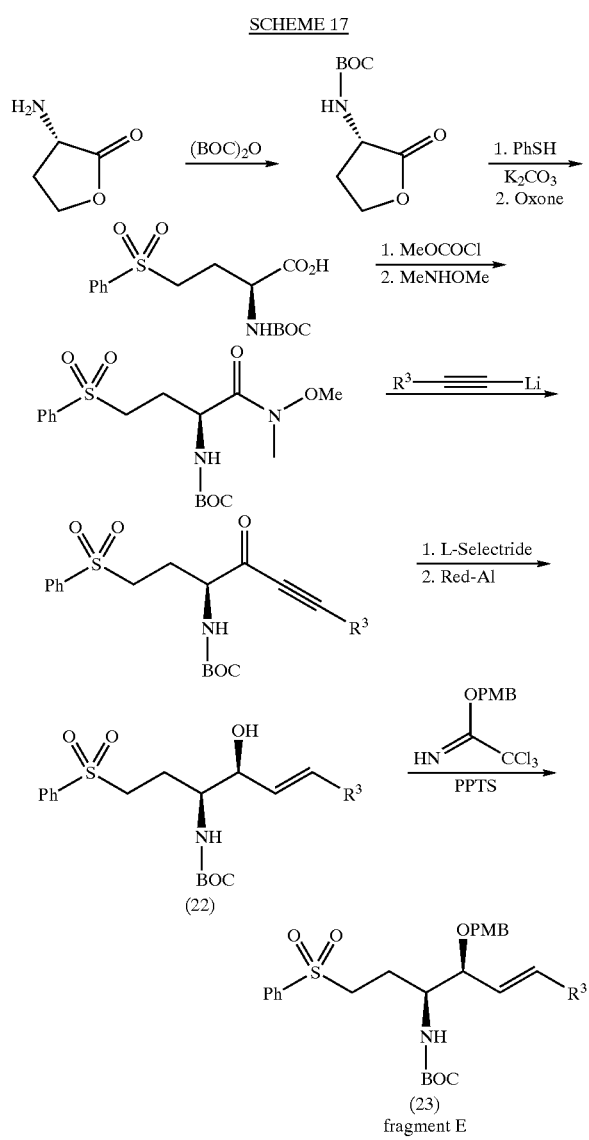

The (L)-homoserine lactone is first N-protected, for example as the tert-butoxycarbonyl (BOC), and the lactone is opened by nucleophilic displacement with thiophenol and base. The sulfide produced is oxidized to the sulfone, for example using potassium peroxymonosulfate. The acid is then converted into the Weinreb amide through the mixed anhydride formed with methyl chloroformate and base by treatment with N,O-dimethylhydroxylamine. The $R^3$ group is introduced by addition of the lithium acetylide to produce the acetylenic ketone. For example, use of lithium phenylacetylide results in ultimate production of the laulimalide lactam wherein $R^3$ is phenyl. Successive reduction using L-Selectride and Red-Al provides intermediate (22), which is converted into fragment E by protection of the alcohol as the PMB ether, for example using PMB trichloroacetimidate and an acid catalyst such as pyridinium p-toluenesulfonate (PPTS).

In other embodiments of the invention, variants of fragment E wherein $R^2$ is H or alkoxy are prepared starting from intermediate (2) using the methods described above for fragments A and C.

Formulation

Typically, the inventive compound is part of a composition comprising the compound itself and a pharmaceutically acceptable carrier. Optionally, the composition may include one or more additional microtubule-stabilizing agents. Representative examples of other microtubule-stabilizing agents include but are not limited to: taxanes (e.g., paclitaxel and docetaxel), epothilone, campothecin, eleutherobin, sarcodictyins, discodermolide, and derivatives thereof. Formulations for taxanes are described by, for example, PCT publication no. WO 99/62510, which is incorporated herein by reference in its entirety.

When the composition is used to psoriasis and dermatitis, the composition optionally may contain therapeutically effective amount of one or more compounds that are used to treat psoriasis and dermatitis including but not limited to: cyclosporine; methotrexate; tamoxifen; forskolin and analogs; tar derivatives; steroids; vitamin A and its derivatives; vitamin D and its derivatives including 1-alpha-hydroxyl-cholecalciferol, 1,25-dihydrlxyl-cholecalciferol, 24,25-dihydroxy-cholecalciferol, 1,24-dihydroxy-cholecalciferol and calcipotriol (MC 903); and beta agonists such as terbutaline.

A wide variety of carriers may be selected of either polymeric or non-polymeric origin which may be biodegradable or non-biodegradable. Representative examples of biodegradable compositions include albumin, collagen, gelatin, hyaluronic acid, starch, cellulose (methylcellulose, hydroxypropylcellulose, hydroxypropylmethylcellulose, hydroxyethylcellulose, carboxymethylcellulose, cellulose acetate phthalate, cellulose acetate succinate, hydroxypropylmethylcellulose phthalate), casein, dextrans, polysaccharides, fibrinogen, poly(D,L-lactide), poly(D,L-lactide-co-glycolide), poly(glycolide), poly(hydroxybutyrate), poly(alkylcarbonate) and poly(orthoesters), polyesters, poly hydroxyvaleric acid), polydioxanone, poly(ethylene terephthaiate), poly(malic acid), poly(tartronic acid), polyanhydrides, polyphosphazenes, poly(amino acids) and their copolymers (see generally, Illum, L., Davids, S. S. (eds.) "Polymers in Controlled Drug Delivery" Wright, Bristol, 1987; Arshady, J. Controlled Release 17:1–22 (1991); Pitt, Int. J. Phar. 59: 173–196 (1990); Holland et al. J. Controlled Release 4:155–180 (1986). Representative examples of nondegradable polymers include poly(ethylene-vinyl acetate) ("EVA") copolymers, silicone rubber, acrylic polymers (polyacrylic acid, polymethylacrylic acid, polymethylmethacrylate, polyalkylcynoacrylate), polyethylene, polyproplene, polyamides (nylon 6,6), polyurethane, poly(ester urethanes), poly(ether urethanes), poly(ester urea), polyethers (poly(ethylene oxide), poly(propylene oxide), Pluronics and poly(tetramethylene glycol)), silicone rubbers and vinyl polymers (polyvinylpyrrolidone, poly(vinyl alcohol), poly(vinyl acetate phthalate). Polymers may also be developed which are either anionic (e.g., alginate, carrageenin, carboxymethyl cellulose and poly(acrylic acid)), or cationic (e.g., chitosan, poly-L-lysine, polyethylenimine, and poly (allyl amine)) (see generally, Dunn et al. J. Applied Polymer Sci. 50:353–365 (1993); Cascone et al., J. Materials Sci.: Materials in Medicine 5: 770–774 (1994); Shiraishi et al., Biol. Pharm. Bull. 16(11): 1164–1168 (1993); Thacharodi and Rao, Int'l J. Pharm. 120: 115–118 (1995); Miyazaki et al., Int'l J. Pharm. 118: 257–263 (1995)). Particularly preferred polymeric carriers include poly(ethylene-vinyl acetate), poly (D, L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, copolymers of poly (caprolactone) or poly (lactic acid) with a polyethylene glycol (e.g., MePEG), and blends thereof.

Polymeric carriers can be fashioned in a variety of forms, with desired release characteristics and/or with specific desired properties. For example, polymeric carriers may be fashioned to release a therapeutic agent upon exposure to a specific triggering event such as pH (see e.g., Heller et al., "Chemically Self-Regulated Drug Delivery Systems," in *Polymers in Medicine III*, Elsevier Science Publishers B. V., Amsterdam, 1988, pp. 175–188; Kang et al., *J Applied Polymer Sci.* 48: 343–354 (1993); Dong et al., *J. Controlled Release* 19: 171–178 (1992); Dong and Hoffman, *J. Controlled Release* 15: 141–152 (1991); Kim et al., *J. Controlled Release* 28: 143–152 (1994); Cornejo-Bravo et al., *J. Controlled Release* 33:223–229 (1995); Wu and Lee, *Pharm. Res* 10(10): 1544–1547 (1993); Serres et al., *Pharm. Res* 13(2): 196–201 (1996); Peppas, "Fundamentals of pH- and Temperature-Sensitive Delivery Systems," in Gurny et al. (eds.), Pulsatile Drug Delivery, Wissenschaftliche Verlagsgesellschaft GmbH, Stuttgart, 1993, pp. 41–55; Doelker, "Cellulose Derivatives," 1993, in Peppas and Langer (eds.), Biopolymers 1, Springer-Verlag, Berlin). Representative examples of pH-sensitive polymers include poly(acrylic acid) and its derivatives (including for example, homopolymers such as poly(aminocarboxylic acid); poly(acrylic acid); poly(methyl acrylic acid), copolymers of such homopolymers, and copolymers of poly(acrylic acid) and acrylmonomers such as those discussed above. Other pH sensitive polymers include polysaccharides such as cellulose acetate phthalate; hydroxypropylmethylcellulose phthalate; hydroxypropylmethylcellulose acetate succinate; cellulose acetate trimellilate; and chitosan. Yet other pH sensitive polymers include any mixture of a pH sensitive polymer and a water soluble polymer.

Likewise, polymeric carriers can be fashioned which are temperature sensitive (see e.g., Chen et al., "Novel Hydrogels of a Temperature-Sensitive Pluronic Grafted to a Bioadhesive Polyacrylic Acid Backbone for Vaginal Drug Delivery," in *Proceed. Intern. Symp. Control. Rel. Bioact. Mater,* 22:167–168, Controlled Release Society, Inc., 1995; Okano, "Molecular Design of Stimuli-Responsive Hydrogels for Temporal Controlled Drug Delivery," in *Proceed. Intern. Symp. Control. Rel. Bioact. Mater,* 22: 111–112, Controlled Release Society, Inc., 1995; Johnston et al., *Pharm. Res.* 9(3): 425–433 (1992); Tung, *Int'l J Pharm.* 107: 85–90 (1994); Harsh and Gehrke, *J. Controlled Release* 17: 175–186 (1991); Bae et al., *Pharm. Res* 8(4): 531–537 (1991); Dinarvand and D'Emanuele, *J. Controlled Release* 36: 221–227 (1995); Yu and Grainger, "Novel Thermosensitive Amphiphilic Gels: Poly N-isopropylacrylamide-co-sodium acrylate-co-n-N-alkylacrylamide Network Synthesis and Physicochemical Characterization," Dept. of Chemical & Biological Sci., Oregon Graduate Institute of Science & Technology, Beaverton, Oreg., pp. 820–821; Zhou and Smid, "Physical Hydrogels of Associative Star Polymers," Polymer Research Institute, Dept. of Chemistry, College of Environmental Science and Forestry, State Univ. of New York, Syracuse, N.Y., pp. 822–823; Hoffman et al., "Characterizing Pore Sizes and Water 'Structure' in Stimuli-Responsive Hydrogels," Center for Bioengineering, Univ. of Wash., Seattle, Wash., p. 828; Yu and Grainger, "Thermosensitive Swelling Behavior in Crosslinked N-isopropylacrylamide Networks: Cationic, Anionic and Ampholytic Hydrogels," Dept. of Chemical & Biological Sci. Oregon Graduate Institute of Science & Technology, Beaverton, Oreg., pp. 829–830; Kim et al., *Pharm. Res* 9(3): 283–290 (1992); Bae et al., *Pharm. Res* 8(5): 624–628 (1991); Kono et al., *J Controlled Release* 30: 69–75 (1994); Yoshida et al. *J Controlled Release* 32: 97–102 (1994); Okano et al., *J Controlled Release* 36: 125–133 (1995); Chun and Kim, *J Controlled Release* 38: 39–47 (1996); D'Emanuele and Dinarvand. *Int. J. Pharm.* 118: 237–242 (1995); Katono et al., *J. Controlled Release* 16: 215–228 (1991); Hoffman, "Thermally Reversible Hydrogels Containing Biologically Active Species," in Migliaresi et al., (eds.), *Polymers in Medicine III*, Elsevier Science Publishers B. V., Amsterdam, 1988, pp. 161 167; Hoffman, "Applications of Thermally Reversible Polymers and Hydrogels in Therapeutics and Diagnostics," in Third International Symposium on Recent Advances in Drug Delivery Systems, Salt Lake City, Utah, Feb. 24–27, 1987, pp. 297–305; Gutowska et al., *J. Controlled Release* 22: 95–104 (1992); Palasis and Gehrke, *J. Controlled Release* 18: 1–12 (1992); Paavola et al. *Pharm. Res* 12(12): 1997–2002 (1995).

Representative examples of thermogelling polymers, and their gelatin temperature (LCST 0° C.) include homopolymers such as poly(N-methyl-N-n-propylacrylamide), 19.8; poly(N-n-propylacrylamide), 21.5; poly(N-methyl-N-isopropylacrylamide), 22.3; poly(N-n-propylmethacrylamide), 28.0; poly(N-isopropylacrylamide), 30.9; poly(N-n-diethylacrylamide), 32.0; poly(N-isopropylmethacrylamide), 44.0; poly(N-cyclopropylacrylamide), 45.5; poly(N-ethylmethyacrylamide), 50.0; poly(N-methyl-N-ethylacrylamide), 56.0; poly(N-cyclopropylmethacrylamide), 59.0; poly(N-ethylacrylamide), 72.0. Moreover thermogelling polymers may be made by preparing copolymers between (among) monomers of the above, or by combining such homopolymers with other water soluble polymers such as acrylmonomers (e.g., acrylic acid and derivatives thereof such as methylacrylic acid, acrylate and derivatives thereof such as butyl methacrylate, acrylamide, and N-n-butyl acrylamide).

Other representative examples of thermogelling polymers include cellulose ether derivatives such as hydroxypropyl cellulose, 41° C.; methyl cellulose, 55° C.; hydroxypropylmethyl cellulose, 66° C.; and ethylhydroxyethyl cellulose, and Pluronics such as F-127, 10–15° C.; L-122, 19° C.; L-92, 26° C.; L-81, 20° C.: and L-61, 24° C.

A wide variety of forms may be fashioned by the polymeric carriers of the present invention, including for example, rod-shaped devices, pellets, slabs, or capsules (see e.g., Goodell et al., *Am. J. Hosp. Pharm.* 43: 1454–1461 (1986); Langer et al., "Controlled release of macromolecules from polymers". in Biomedical Polymers, *Polymeric Materials and Pharmaceuticals For Biomedical Use*: Goldberg, E. P., Nakagim. A. (eds.) Academic Press, pp. 113–137, 1980; Rhine et al., *J Pharm. Sci.* 69: 265–270 (1980); Brown et al., *J. Pharm. Sci.* 72: 1181–1185 (1983); and Bawa et al., *J. Controlled Release* 1: 259–267 (1985)). Therapeutic agents may be linked by occlusion in the matrices of the polymer, bound by covalent linkages, or encapsulated in microcapsules. Within certain preferred embodiments of the invention, pharmaceutical compositions are provided in non-capsular formulations such as microspheres (ranging from nanometers to micrometers in size), pastes, threads of various size, films and sprays. Preferably, pharmaceutical compositions of the present invention are fashioned in a manner appropriate to the intended use. Within certain aspects of the present invention, the pharmaceutical composition should be biocompatible, and release one or more therapeutic agents over a period of several days to months. For example, "quick release" or "burst" pharmaceutical compositions are provided that release greater than 10%, 20%, or 25% (w/v) of a therapeutic agent over a period of 7 to 10 days. Such "quick release" compositions should, within certain embodiments, be capable of releasing chemotherapeutic levels (where applicable) of a desired agent. Within other embodiments, "low release" pharmaceutical compositions are provided that release less than 1% (w/v) of a therapeutic agent over a period of 7 to 10 days. Further, pharmaceutical compositions of the present invention should preferably be stable for several months and capable of being produced and maintained under sterile conditions.

Within certain aspects of the present invention, pharmaceutical compositions may be fashioned in any size ranging from 50 nm to 500 μm, depending upon the particular use. Alternatively, such compositions may also be readily applied as a "spray", which solidifies into a film or coating. Such sprays may be prepared from microspheres of a wide array of sizes, including for example, from 0.1 μm to 3 μm, from 10 μm to 30 μm, and from 30 μm to 100 μm.

Pharmaceutical compositions of the present invention may also be prepared in a variety of "paste" or gel forms. For example, within one embodiment of the invention, pharmaceutical compositions are provided which are liquid at one temperature (e.g., temperature greater than 37° C. such as 40° C., 45° C., 50° C., 55° C., or 60° C.), and solid or semi-solid at another temperature (e.g., ambient body temperature, or any temperature lower than 37° C.). Such "thermopastes" may be readily made given the disclosure provided herein.

Within yet other aspects of the invention, the pharmaceutical compositions of the present invention may be formed as a film, wrap or barrier. Preferably, such films are generally less than 5, 4, 3, 2, or 1 mm thick, more preferably less than 0.75 mm or 0.5 mm thick, and most preferably less than 500 μm to 100 μm thick. Such films are preferably flexible with a good tensile strength (e.g., greater than 50, preferably greater than 100, and more preferably greater than 150 or 200 N/cm²), good adhesive properties (i.e., readily adheres to moist or wet surfaces), and have controlled permeability.

Within further aspects of the invention, the pharmaceutical compositions may be formulated for topical application. Representative examples include: ethanol; mixtures of ethanol and glycols (e.g., ethylene glycol or propylene glycol); mixtures of ethanol and isopropyl myristate or ethanol, isopropyl myristate and water (e.g., 55:5:40); mixtures of ethanol and eineol or D-limonene (with or without water); glycols (e.g., ethylene glycol or propylene glycol) and mixtures of glycols such as propylene glycol and water, phosphatidyl glycerol, dioleoylphosphatidyl glycerol, ethyldiglycol (i.e., Transcutol®), or terpinolene; mixtures of isopropyl myristate and 1-hexyl-2-pyrrolidone, N-dodecyl-2-piperidinone or 1-hexyl-2-pyrrolidone. Other excipients may also be added to the above, including for example, acids such as oleic acid and linoleic acid, and soaps such as sodium lauryl sulfate. A preferred embodiment would include buffered saline or water, antimicrobial agents (e.g., methylparaben, propylparaben), carrier polymer(s), such as celluloses (e.g., hydroxyethylcellulose) and (a) penetration or permeation enhancer(s) (e.g., ethoxydiglycol—Transcutol®, isopropyl myristate, ethylene glycol, 1 hexyl-2-pyrrolidone, D-limonene). For a more detailed description of the above, see generally, Hoelgaard et al., *J. Contr. Rel.* 2: 111 (1985); Liu et al., *Pharm. Res.* 5: 938 (1991); Roy et al., *J. Pharm. Sci.* 83: 126 (1991); Ogiso et al., *J. Pharm. Sci.* 84: 482 (1995); Sasaki et al., *J. Pharm. Sci.* 80: 533 (1991); Okabe et al., *J. Contr. Rel.* 32: 243 (1994); Yokomizo et al., *J. Contr. Rel.* 38: 267 (1996); Yokomizo et al., *J. Contr. Rel.* 42: 37 (1996); Mond et al., *J. Contr. Rel.* 33: 72 (1994); Michniak et al., *J. Contr. Rel.* 32: 147 (1994); Sasaki et al., *J. Pharm. Sci.* 80: 533 (1991); Baker & Hadgraft, *Pharm. Res.* 12: 993 (1995); Jasti et al., AAPS Proceedings, 1996; Lee et al., AAPS Proceedings, 1996; Ritschel et al., *Skin Pharmacol.* 4: 235 (1991); and McDaid & Deasy, *Int. J. Pharm.* 133: 71 (1996).

Within certain embodiments of the invention, the pharmaceutical compositions may also comprise additional ingredients such as surfactants (e.g., 20 Pluronics such as F-127, L-122, L-92, L S 1, and L-61).

Within further aspects of the present invention, polymeric carriers are provided which are adapted to contain and release a hydrophobic compound such as a compound of the present invention. Typically, the carrier contains the hydrophobic compound in combination with a carbohydrate, protein or polypeptide. Within certain embodiments the polymeric carrier contains or comprises regions, pockets, or granules of one or more hydrophobic compounds. For example, within one embodiment of the invention, hydrophobic compounds may be incorporated within a matrix that is then incorporated within the polymeric carrier. A variety of matrices can be utilized in this regard, including for example, carbohydrates and polysaccharides such as starch, cellulose, dextran, methylcellulose, and hyaluronic acid, proteins or polypeptides such as albumin, collagen and gelatin. Within alternative embodiments, hydrophobic compounds may be contained within a hydrophobic core, and this core contained within a hydrophilic shell.

Other carriers that may likewise be utilized to contain and deliver the compounds described herein include: hydroxypropyl β cyclodextrin (Cserhati and Hollo, *Int. J. Pharm.* 108: 69–75 (1994)): liposomes (see e.g., Sharma et al., *Cancer Res* 53: 5877–5881 (1993); Sharma and Straubinger, *Pharm. Res.* 11(60): 889–896 (1994); WO 93/18751; U.S. Pat. No. 5,242,073), liposome/gel (WO 94/26254), nanocapsules (Bartoli et al., *J. Microencapsulation* 7(2): 191–197 (1990), micelles (Alkan-Onyuksel et al., *Pharm. Res* 11(2): 206–212 (1994)), implants (Jampel et al., *Invest. Ophthalm. Vis. Science* 31(11): 3076–3083 (1993); Walter et al., *Cancer Res.* 54: 22017–2212 (1994)), nanoparticles (Violante and Lanzafame PAACR), nanoparticles-modified (U.S. Pat. No. 5,145,684), nanoparticles (surface modified) (U.S. Pat. No. 5,399,363), micelle (surfactant) (U.S. Pat. No. 5,403,858), synthetic phospholipid compounds (U.S. Pat. No. 4,534,899), gas borne dispersion (U.S. Pat. No. 5,301,464), liquid emulsions, foam, spray, gel, lotion, cream, ointment, dispersed vesicles, particles or droplets, solid- or liquid-aerosols, microemulsions {U.S. Pat. No. 5,330,756), polymeric shell (nano- and micro-capsule) (U.S. Pat. No. 5,439,686), emulsion (Tarr et al., *Pharm Res.* 4: 62–165, 1987), nanospheres (Hagan et al., *Proc. Intern. Symp. Control Rel. Bioact. Mater.* 22, 1995; Kwon et al., *Pharm Res* 12(2): 192–195; Kwon et al., *Pharm. Res.* 10(7): 970–974; Yokoyama et al., *J. Contr. Rel.* 32: 269–277 (1994); Gref et al., *Science* 263: 1600–1603 (1994); Bazile et al., *J. Pharm. Sci.* 84: 493–498 (1994)), implants (U.S. Pat. No. 4,882, 168), wraps, films and inhaled formulations.

Methods of Use

In general, methods of using the compounds of the present invention comprise administering to a subject in need thereof a therapeutically effective amount of a compound of the present invention. Diseases that may be treated with the compounds of the present invention are those that are characterized by cellular hyperproliferation, such as cancers, tumors, and inflammatory disorders. Illustrative examples of inflammatory disorders include, for example, atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis, irritant dermatitis, allergic dermatitis), periodontal disease (i.e., periodontitis), polycystic kidney disease, and type I diabetes.

Other examples of inflammatory diseases include vasculitis (e.g., Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic).

Because the use of microtubule-stabilizing agents such as the laulimalides, taxanes, epothilones, discodermolide, eleutherobin, and the like, to treat inflammatory disorders are not as well documented as the use of microtubule-stabilizing agents to treat cancers and tumors, three representative examples of inflammatory disorders are discussed in greater detail below.

Psoriasis and Eczema

Utilizing the agents, compositions and methods provided herein, a wide variety of inflammatory skin diseases can be readily treated or prevented. For example, within one embodiment of the invention an inflammatory skin disease such as psoriasis or eczema may be treated or prevented by delivering to a site of inflammation (or a potential site of inflammation) an agent that inhibits microtubule function. Briefly, skin cells are genetically programmed to follow two possible programs—normal growth or wound healing. In the normal growth pattern, skin cells are created in the basal cell layer and then move up through the epidermis to the skin surface. Dead cells are shed from healthy skin at the same rate new cells are created. The turnover time (i.e., time from cell birth to death) for normal skin cells is approximately 28 days. During wound healing, accelerated growth and repair is triggered resulting in rapid turnover of skin cells (to replace and repair the wound), increased blood supply (to meet the increased metabolic needs associated with growth) and localized inflammation.

In many respects, psoriasis is similar to an exaggerated wound healing process where skin cells (called "keratinocytes") are created and pushed to the skin surface in as little as 2–4 days. Psoriasis occurs when skin cells hyperproliferate and the surface skin cannot shed the dead cells fast enough. The excess keratinocytes build up and form elevated, scaly lesions. This growth is supported by new blood vessels in the dermis (the support tissue beneath the epidermis) that are established to provide the nutrients necessary to support the hyperproliferating keratinocytes. At the same time, lymphocytes, neutrophils and macrophage invade the tissue, creating inflammation, swelling and soreness, and potentially producing growth factors that augment the rapid proliferation of the keratinocytes. All these cells (keratinocytes, vascular endothelial cells and white blood cells) produce tissue degrading enzymes or proteinases that aid in the progression of the disease and the destruction of surrounding tissue.

Utilizing the compositions of the present invention, inflammatory skin lesions may be readily treated. In particular, the microtubule-stabilizing agent is administered directly to the site of inflammation (or a potential site of inflammation), in order to treat or prevent the disease. The one or more microtubule-stabilizing stabilizing agents may be delivered as a composition along with a polymeric carrier, or in a liposome, cream or ointment formulation as discussed previously. Within preferred embodiments of the invention, the agents or compositions are delivered either topically, or by subcutaneous administration. An effective therapy for psoriasis will achieve at least one of the following: decrease the number and severity of skin lesions, decrease the frequency or duration of active disease exacerbations, increase the amount of time spent in remission (i.e., periods when the patient is symptom-free) and/or decrease the severity or duration of associated symptoms (e.g., joint pain and swelling, axial skeletal pain, bowel symptoms). Clinically the treatment will result in a reduction in the size or number of skin lesions, diminution of cutaneous symptoms (pain, burning and bleeding of the affected skin) and/or a reduction in associated symptoms (e.g., joint redness, heat, swelling, diarrhea, abdominal pain). Pathologically an microtubule-stabilizing agent will produce at least one of the following: inhibition of keratinocyte proliferation, reduction of skin inflammation (for example, by impacting on: attraction and growth factors, antigen presentation, production of reactive oxygen species and matrix metalloproteinases), and inhibition of dermal angiogenesis.

The microtubule-stabilizing agent can be administered in any manner sufficient to achieve the above end points, but preferred methods include topical and systemic administration. Patients with localized disease can be administered a topical cream, ointment or emollient applied directly to the psoriatic lesions. For example, a topical cream containing 0.001% to 10% of an inventive compound by weight is administered depending upon severity of the disease and the patient's response to treatment. In a preferred embodiment, a topical preparation containing an inventive compound at 0.01% to 1% by weight is administered to psoriatic lesions. Alternatively, direct intracutaneous injection of an inventive compound in a suitable pharmaceutical vehicle can be used for the management of individual lesions. In patients with widespread disease or extracutaneous symptoms (e.g., psoriatic arthritis, Reiter's syndrome, associated spondylitis, associated inflammatory bowel disease) systemic treatment can be administered. For example, intermittent treatments with an intravenous formulation can be administered at a dose of 10 to 75 mg/m$^2$ of a compound of the present invention depending upon therapeutic response and patient tolerance. An equivalent oral preparation would also be suitable for this indication.

Other dermatological conditions that can also benefit from topical microtubule-stabilizing agents include: eczematous disease (atopic dermatitis, contact dermatitis, eczema), immunobullous disease, pre-malignant epithelial tumors, basal cell carcinoma, squamous cell carcinoma, keratocanthoma, malignant melanoma and viral warts. Topical creams, ointments, and emollients containing 0.001% to 10% inventive compound by weight can be suitable for the management of these conditions.

Multiple Sclerosis

Microtubule-stabilizing agents may be utilized to treat or prevent chronic inflammatory neurological disorders, such as multiple sclerosis. Briefly, multiple sclerosis ("MS") is a devastating demyelinating disease of the human central nervous system. Although its etiology and pathogenesis is not known, genetic, immunological and environmental factors are believed to play a role. In the course of the disease, there is a progressive demyelination in the brain of MS patients resulting in the loss of motor function. Although the exact mechanisms involved in the loss of myelin are not understood, there is an increase in astrocyte proliferation and accumulation in the areas of myelin destruction. At these sites, there is macrophage-like activity and increased protease activity which is at least partially responsible for degradation of the myelin sheath.

Microtubule-stabilizing agent of the present invention can be administered to the site of inflammation (or a potential site of inflammation), in order to treat or prevent the disease. Such agents may, within certain embodiments, be delivered as a composition along with a polymeric carrier, or in a liposome formulation as previously. Within certain embodiments of the invention, the agents or compositions may be administered orally, intravenously, or by direct administration (preferably with ultrasound, CT, fluoroscopic, MRI or endoscopic guidance) to the disease site. An effective therapy for multiple sclerosis will accomplish one or more of the following: decrease the severity of symptoms; decrease the duration of disease exacerbations; increase the frequency and duration of disease remission/symptom-free periods; prevent fixed impairment and disability; and/or prevent/attenuate chronic progression of the disease. Clinically, this would result in improvement in visual symptoms (visual loss, diplopia), gait disorders (weakness, axial instability, sensory loss, spasticity, hyperreflexia, loss of dexterity), upper extremity dysfunction (weakness, spasticity, sensory loss), bladder dysfunction (urgency, incontinence, hesitancy, incomplete emptying), depression, emotional lability, and cognitive impairment. Pathologically the treatment reduces one or more of the following, such as myclin loss, breakdown of the blood-brain barrier, perivascular infiltration of mononuclear cells, immunologic abnormalities, gliotic scar formation and astrocyte proliferation, metalloproteinase production, and impaired conduction velocity.

The microtubule-stabilizing agent can be administered in any manner sufficient to achieve the above endpoints. However, preferred methods of administration include intravenous, oral, or subcutaneous, intramuscular or intrathecal injection. The microtubule-stabilizing agent can be administered as a chronic low dose therapy to prevent disease progression, prolong disease remission or decrease symptoms in active disease. Alternatively, the therapeutic agent can be administered in higher doses as a "pulse" therapy to induce remission in acutely active disease. The minimum dose capable of achieving these endpoints can be used and can vary according to patient, severity of disease, formulation of the administered agent, and route of administration. For example, preferred embodiments would include 10 to 75 Mg/m$^2$ of an inventive compound once every 1 to 4 weeks, 10 to 75 mg/m$^2$ daily, as tolerated, or 10 to 175 mg/m$^2$ once weekly, as tolerated or until symptoms subside.

Arthritis

Inflammatory arthritis is a serious health problem in developed countries, particularly given the increasing number of aged individuals. For example, one form of inflammatory arthritis, rheumatoid arthritis ("RA") is a multisystem chronic, relapsing, inflammatory disease of unknown cause. Although many organs can be affected, RA is basically a severe form of chronic synovitis that sometimes leads to destruction and ankyiosis of affected joints (Robbins Pathological Basis of Disease, by R. S. Cotran, V. Kumar, and S. L. Robbins, W. B. Saunders Co., 1989). Pathologically, the disease is characterized by a marked thickening of the synovial membrane which forms villous projections that extend into the joint space, multilayering of the synoviocyte lining (synoviocyte proliferation), infiltration of the synovial membrane with white blood cells (macrophages, lymphocytes, plasma cells, and lymphoid follicles; called an "inflammatory synovitis"), and deposition of fibrin with cellular necrosis within the synovium. The tissue formed as a result of this process is called pannus and, eventually the pannus grows to fill the joint space. The pannus develops an extensive network of new blood vessels through the process of angiogenesis that is essential to the evolution of the synovitis. The release of digestive enzymes (matrix metalloproteinases such as collagenase, stromelysin, and the like) and other mediators of the inflammatory process (e.g., hydrogen peroxide, superoxides, lysosomal enzymes, and products of arachadonic acid metabolism) from the cells of the pannus tissue leads to the progressive destruction of the cartilage tissue. The pannus invades the articular cartilage leading to erosions and fragmentation of the cartilage tissue. Eventually there is erosion of the subchondral bone with fibrous ankylosis and ultimately bony ankylosis, of the involved joint. It is generally believed, but not conclusively proven, that RA is an autoinmmune disease, and that many different arthrogenic stimuli activate the immune response in the immunogenetically susceptible host. Both exogenous infectious agents (Ebstein-Barr virus, rubella virus, cytomegalovirus, herpes virus, human T-cell lymphotropic virus, Mycoplasma, and others) and endogenous proteins (collagen, proteoglycans, altered immunoglobulins) have been implicated as the causative agent that triggers an inappropriate host immune response. Regardless of the inciting agent, autoimmunity plays a role in the progression of the disease. In particular, the relevant antigen is ingested by antigen-presenting cells (macrophages or dendritic cells in the synovial membrane), processed, and presented to T lymphocytes. The T cells initiate a cellular immune response and stimulate the proliferation and differentiation of B lymphocytes into plasma cells. The end result is the production of an excessive inappropriate immune response directed against the host tissues (e.g., antibodies directed against type II collagen, antibodies directed against the Fc portion of autologous IgG (called "Rheumatoid Factor")). This further amplifies the immune response and hastens the destruction of the cartilage tissue. Once this cascade is initiated numerous mediators of cartilage destruction are responsible for the progression of rheumatoid arthritis.

Thus, within one aspect of the present invention, methods are provided for treating or preventing inflammatory arthritis (e.g., rheumatoid arthritis) comprising the step of administering to a patient a therapeutically effective amount of an microtubule-stabilizing agent. Inflammatory arthritis includes a variety of conditions including, but not limited to, rheumatoid arthritis, systemic lupus erythematosus, systemic sclerosis (scleroderma), mixed connective tissue disease, Sjogren's syndrome, ankylosing spondylitis, Behcet's syndrome, sarcoidosis, and osteoarthritis—all of which feature inflamed, painful joints as a prominent symptom.

Within a preferred embodiment of the invention, microtubule-stabilizing agents may be administered directly to a joint by intra-articular injection, as a surgical paste or administered by another route, e.g., systemically or orally. Such agents may, within certain embodiments, be delivered as a composition along with a polymeric carrier, or in a liposome formulation as discussed previously.

An effective microtubule-stabilizing therapy for inflammatory arthritis will accomplish one or more of the following: (i) decrease the severity of symptoms (pain, swelling and tenderness of affected joints; morning stiffness, weakness, fatigue, anorexia, weight loss); (ii) decrease the severity of clinical signs of the disease (thickening of the joint capsule, synovial hypertrophy, joint effusion, soft tissue contractures, decreased range of motion, ankylosis and fixed joint deformity); (iii) decrease the extra-articular manifestations of the disease (rheumatic nodules, vasculitis, pulmonary nodules, interstitial fibrosis, pericarditis, episcleritis, iritis, Felty's syndrome, osteoporosis); (iv) increase the frequency and duration of disease remission/symptom-free periods; (v) prevent fixed impairment and disability; and/or (vi) prevent/attenuate chronic progression of the disease. Pathologically, an effective ricrotubule-stabilizing therapy for inflammatory arthritis will produce at least one of the following: (i) decrease the inflammatory response, (ii) disrupt the activity of inflammatory cytokines (such as IL-I, TNFa, FGF, VEGF), (iii) inhibit synoviocyte proliferation, (iv) block matrix metalloproteinase activity, and/or (v) inhibit angiogenesis. An microtubule-stabilizing agent will be administered systemically (orally, intravenously, or by intramuscular or subcutaneous injection) in the minimum dose to achieve the above mentioned results. For patients with only a small number of joints affected, or with disease more prominent in a limited number of joints, the microtubule-stabilizing agent can be directly injected (intra-articular injection) into the affected joints. The microtubule-stabilizing agent can be administered in any manner sufficient to achieve the above endpoints. However, preferred methods of administration include intravenous, oral, or subcutaneous, intramuscular or intra-articular injection. The microtubule-stabilizing agent can be administered as a chronic low dose therapy to prevent disease progression, prolong disease remission, or decrease symptoms in active disease.

Alternatively, the therapeutic agent can be administered in higher doses as a "pulse" therapy to induce remission in acutely active disease. The minimum dose capable of achieving these endpoints can be used and can vary according to patient, severity of disease, formulation of the administered agent, and route of administration. For example, preferred embodiments would include 10 to 75 mg/m$^2$ of an inventive compound once every 1 to 4 weeks, 10 to 75 mg/m$^2$ daily, as tolerated, or 10 to 175 mg/m$^2$ once weekly, as tolerated or until symptoms subside.

A detailed description of the invention having been provided above, the following examples are given for the purpose of illustrating the present invention and shall not be construed as being a limitation on the scope of the invention or claims.

EXAMPLE 1

Laulimalide

A sample of laulimalide-producing sponge (*Cacospongis mycofijiensis*, or *Hyatella* sp.) is lyophilized and then ground to a powder. The powder is extracted three times by stirring with CH$_2$Cl$_2$/isopropanol for 24 hours at ambient temperature followed by centrifugation and decanting the supernatant. The extracts are combined and evaporated under reduced pressure at a temperature below 50° C. The residue is dissolved in 9:1 methanol/water and washed three times with equal volumes of hexanes. The methanolic solution is then diluted with water to a final water concentration of 20% and extracted three times with equal volumes of toluene. The toluene extracts are combined and evaporated to dryness under reduced pressure at a temperature below 100° C. The residue is dissolved in a minimal amount of CH$_2$Cl$_2$ and chromatographed on silica gel using ether as eluent. Fractions are analyzed by LC/MS, [M+H]$^+$ m/z=515.6, and laulimalide-containing fractions are pooled and evaporated, then chromatographed a second time on silica gel using 3:1 methyl tert-butyl ether/hexanes+1% isopropanol as eluent. Fractions are analyzed by LC/MS, and laulimalide-containing fractions are pooled and evaporated to provide purified laulimalide.

Alternatively, laulimalide is synthesized according to the method of Paterson et al., "Total synthesis of the microtubule-stabilizing agent (−)-laulimalide," *Org. Letts.* 2001, 3: 3149–3152, which is incorporated herein by reference.

EXAMPLE 2

16,17-desoxylaulimalide

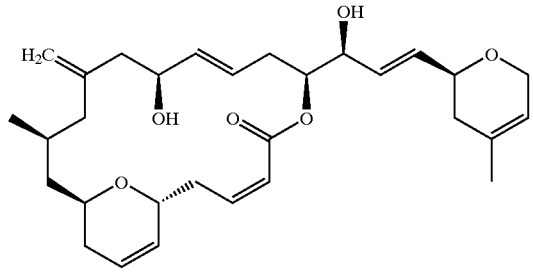

Step 1. A solution of laulimalide (515 mg, 1 mmol) in 10 mL of dichloromethane is cooled on ice and treated sequentially with tert-butyldimethylsilyl trifluoromethanesulfonate (660 mg, 2.5 mmol) and 2,6-lutidine (320 mg, 3 mmol). After stirring for 2 hours, the mixture is poured into sat. aq. NaHCO$_3$ and extracted with ether. The organic extract is dried over MgSO$_4$, filtered, and evaporated to dryness. The product 15,20-bis-(O-tert-butyldimethyl-silyl)-laulimalide is purified by silica gel chromatography.

Step 2. Chopped pieces of magnesium turnings (0.12 g, 5 mmol) are flame-dried in a round bottom flasked under vacuum, and allowed to cool to ambient temperature under an argon atmosphere. Titanocene dichloride (1.25 g, 5 mmol) is added, followed by 25 mL of freshly distilled tetrahydrofuran. The suspension is stirred and degassed by placing under mild vacuum followed by replacement of the atmosphere with argon. Consumption of the magnesium and color change from red to green (ca. 1.5 hours) provides a 0.2 M solution of the deoxygenation reagent. A 6.0 mL aliquot of this solution (1.2 mmol) is transferred to a fresh flask under argon and cooled to −78° C. To this is added a solution of 15,20-bis-(O-tert-butyldimethylsilyl)-laulimalide (60 mg, 81 mmol) in 0.5 mL of THF. After 15 minutes at −78° C., the mixture is poured into ethyl acetate and sat. aq. NaHCO$_3$ and extracted with ethyl acetate. The extract is washed with brine, dried over MgSO$_4$, filtered, and evaporated to dryness. The product 15,20-bis-(O-tert-butyldimethylsilyl)-16,17-desoxylaulimalide is purified by silica gel chromatography.

Step 3. A solution of 15,20-bis-(O-tert-butyldimethylsilyl)-16,17-desoxylaulimalide (60 mg) in 2 mL of dichloromethane is cooled to −15° C. and treated with 0.5 mL of trifluoroacetic acid. The mixture is then warmed to 0° C. and stirred for 2 hours. The mixture is concentrated to dryness, and the residue is chromatographed on silica gel to provide 16,17-desoxylaulimalide. The product is identified by its LC/MS spectrum, [M+H]⁺ m/z=499.3.

EXAMPLE 3

16,17-desoxy-16,17-methylenelaulimalide

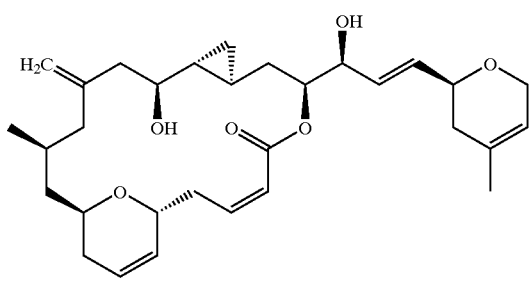

Diuodomethane (0.24 mL, 3.0 mmol) is added dropwise to a solution of 16,17-desoxy-laulimalide (500 mg, 1 mmol) and diethylzinc (1.5 mL of a 1.0 M solution in hexanes) in 5 mL of ether. After 4 hours at ambient temperature, the mixture is diluted with ether and washed successively with 1 N HCl, sat. aq. NaHCO₃, and brine, then dried over MgSO₄, filtered, and evaporated to dryness. The product is purified by silica gel chromatography.

EXAMPLE 4

Laulimalide 15,20-di-(O-methylcarbonate)

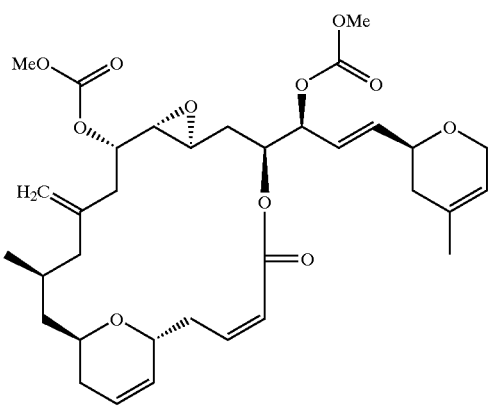

A solution of laulimalide (515 mg, 1 mmol) in 10 mL of dichloromethane is cooled on ice and treated with methyl chloroformate (0.5 mL, 6.5 mmol) and 2,6-lutidine (1.0 mL, 8.6 mmol). After 4 hours, the mixture is poured into sat. aq. NaHCO₃ and extracted with ether. The extract is dried over MgSO₄, filtered, and evaporated to dryness. The product is purified by silica gel chromatography.

EXAMPLE 5

20-O-methyl-laulimalide

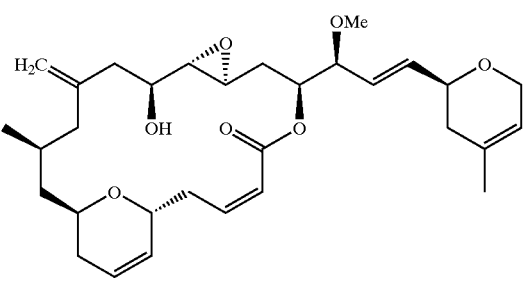

A solution of laulimalide 15,20-di-(O-methylcarbonate) (630 mg, 1 mmol) and tetrakis(triphenylphosphine) palladium (20 mg, 0.017 mmol) in 10 mL of degassed THF is heated at reflux under argon atmosphere. After 4 hours, the mixture is cooled to ambient temperature and evaporated to dryness. The residue is dissolved in 10 mL of methanol containing 1% triethylamine, heated at 50° C. overnight, then evaporated to dryness. The product is purified by silica gel chromatography.

EXAMPLE 6

16,17-desoxy-20-O-methyl-laulimalide

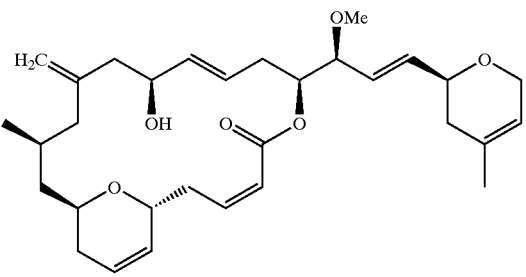

Step 1. A solution of laulimalide 15,20-di-(O-methylcarbonate) (630 mg, 1 mmol) and tetrakis(triphenylphosphine)palladium (20 mg, 0.017 mmol) in 10 mL of degassed THF is heated at reflux under argon atmosphere. After 4 hours, the mixture is cooled to ambient temperature and evaporated to dryness. The product 20-O-methyl-laulimalide 15-O-(methylcarbonate) is purified by silica gel chromatography.

Step 2. A 6.0 mL aliquot of tdeoxygenation reagent solution prepared according to example 2 (1.2 mmol) is transferred to a flask under argon and cooled to −78° C. To this is added a solution of 20-O-methyl-laulimalide 15-O-(methylcarbonate) (48 mg, 81 mmol) in 0.5 mL of THF. After 15 minutes at −78° C., the mixture is poured into ethyl acetate and sat. aq. NaHCO3 and extracted with ethyl acetate. The extract is washed with brine, dried over MgSO4, filtered, and evaporated to dryness. The product 16,17-desoxy-20-O-methyl-laulimalide 15-O-(methylcarbonate) is purified by silica gel chromatography.

Step 3. A solution of 16,17-desoxy-20-O-methyl-laulimalide 15-O-(methylcarbonate) (40 mg) in 5 mL of methanol containing 1% triethylamine is heated at 50° C. overnight, then evaporated to dryness. The product 16,17-desoxy-20-O-methyl-laulimalide is purified by silica gel chromatography.

EXAMPLE 7

N-methoxy-N-methyl-2-(tert-butoxycarbonylamino)-4-(phenylsulfonyl)butyramide

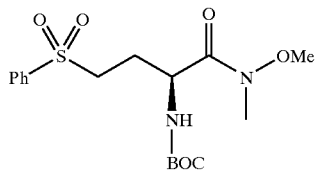

Step 1. A mixture of N-BOC-(L)-homoserine lactone (2.19 g, 10 mmol), benzenethiol (1.10 g, 10 mmol) and potassium carbonate (1.38 g, 10 mmol) in 15 mL of N,N-dimethylformamide is heated at 100° C. for 4 hours. The solution is concentrated under vacuum, and the residue is partitioned between ethyl acetate and 1 N HCl, and the organic extract is washed sequentially with cold 1 N HCl and brine, dried over $MgSO_4$, filtered, and evaporated to dryness. The crude sulfide is dissolved in 50 mL of 4:1 methanol/water and treated with potassium peroxymonosulfate (18.5 g) for 18 hours. The mixture is filtered and the filtrate is partitioned between ethyl acetate and water. The organic phase is dried over $MgSO_4$, filtered, and evaporated to dryness to provide the sulfone acid.

Step 2. A suspension of N,O-dimethylhydroxylamine hydrochloride (3.91 g, 40 mmol) in 23.6 mL of dichloromethane is cooled on ice and treated dropwise with N-methylpiperidine (4.88 mL, 41 mmol) to generate a solution of N,O-dimethylhydroxylamine. A second flask is charged with the sulfone acid from Step 1 above (13.7 g, 40 mmol) and 180 mL of dichloromethane, and cooled to −20° C. N-methylpiperidine (4.88 mL, 41 mmol) is added rapidly, followed by methyl chloroformate (3.1 mL, 40 mmol), keeping the temperature below −12° C. After 2 minutes, the solution of N,O-dimethylhydroxylamine is added. The mixture is warmed to ambient temperature over 4 hours, then cooled again on ice and washed with two 50-mL portions of 0.2 N HCl and two 50-mL portions of 0.5 N NaOH. The solution is washed with brine, dried over $MgSO_4$, filtered, and evaporated to dryness to provide the Weinreb amide.

EXAMPLE 8

(3S,4S)-4-(tert-butoxycarbonylamino)-3-(4-methoxybenzyloxy)-1-phenyl-6-(phenylsulfonyl)-1-hexene

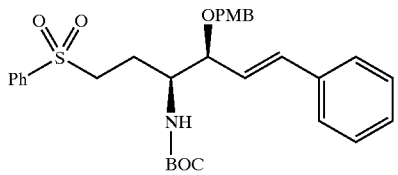

Step 1. A 1.6 M solution of n-butyllithium in hexane (6.25 mL, 10.0 mmol) is added to a −78° C. solution of phenylacetylene (10.2 g, 10.0 mmol) in 40 mL of THF and the mixture is stirred for 1 hour. A solution of N-methoxy-N-methyl-2-(tert-butoxycarbonylamino)-4-(phenylsulfonyl)-butyramide (Example 7, 3.86 g, 10.0 mmol) in 10 mL of THF is added dropwise, and the mixture is stirred for an additional 1 hour at −78° C. before warming to 0° C. and pouring into ice cold 1 N HCl. The phases are separated and the aqueous phase is extracted with ethyl acetate. The organic phases are combined, dried over $MgSO_4$, filtered, and evaporated to dryness. The product ketone is purified by silica gel chromatography.

Step, 2. To a solution of the ketone from Step 1 (4.27 g, 10.0 mmol) in 30 mL of THF at −78° C. is added L-Selectride (15.0 mL of a 1.0 M solution in THF) dropwise. The mixture is stirred for 30 min at −78° C., then quenched with sat. aq. $NH_4Cl$ and extracted with ethyl acetate. The extract is washed with brine, dried over $MgSO_4$, filtered, and evaporated to dryness. The product alkynyl alcohol is purified by silica gel chromatography.

Step 3. Red-Al (1.3 mL of a 65% solution of sodium bis(2-methoxyethoxy)aluminum hydride in toluene, 4.3 mmol) is added dropwise to a solution of the alkynyl alcohol from Step 2 (1.16 g, 2.7 mmol) in 6 mL of THF at −40° C. The mix is then warmed to −20° C., stirred for 1 hour, then treated with 10% aq. Rochelle's salt for 2 hours at ambient temperature. The mixture is extracted with ethyl acetate, and the extract is washed with brine, dried over $MgSO_4$, filtered, and evaporated to dryness. The product alkenyl alcohol is purified by silica gel chromatography.

Step 4. A solution of the alkenyl alcohol from Step 3 (4.29 g, 10 mmol) in dichloromethane (15 mL) is treated with 4-methoxybenzyl trichloroacetimidate (4.25 g, 15 mmol) and pyridinium p-toluenesulfonate (0.15 g) for 3 hours at 0° C. The mixture is then warmed to ambient temperature and stirred for 40 hours, then evaporated under vacuum. The product is isolated by flash chromatography on silica gel.

EXAMPLE 9

(3S,4S)-4-(tert-butoxycarbonylamino)-3-(4-methoxybenzyloxy)-1-phenyl-6-(phenylsulfonyl)-1-hexene

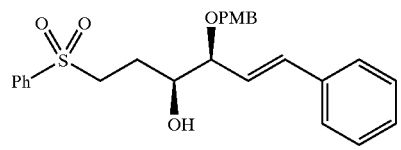

Step 1. A 1.6 M solution of n-butyllithium in hexane (6.25 mL, 10.0 mmol) is added to a −78° C. solution of phenylacetylene (10.2 g, 10.0 mmol) in 40 mL of THF and the mixture is stirred for 1 hour. A solution of N-methoxy-N-methyl-2-hydroxy-4-(phenylsulfonyl)-butyramide (2.87 g, 10.0 mmol) (Ghosh et al., 2001, J. Org. Chem. ***) in 10 mL of THF is added dropwise, and the mixture is stirred for an additional 1 hour at −78° C. before warming to 0° C. and pouring into ice cold 1 N HCl. The phases are separated and the aqueous phase is extracted with ethyl acetate. The organic phases are combined, dried over $MgSO_4$, filtered, and evaporated to dryness. The product ketone is purified by silica gel chromatography.

Step 2. To a solution of the ketone from Step 1 (3.30 g, 10.0 mmol) in 30 mL of THF at −78° C. is added L-Selectride (15.0 mL of a 1.0 M solution in THF) dropwise. The mixture is stirred for 30 min at −78° C., then quenched with sat. aq. $NH_4Cl$ and extracted with ethyl acetate. The extract is washed with brine, dried over $MgSO_4$, filtered, and evaporated to dryness. The product alkynyl alcohol is purified by silica gel chromatography.

Step 3. Red-Al (1.3 mL of a 65% solution of sodium bis(2-methoxyethoxy)aluminum hydride in toluene, 4.3 mmol) is added dropwise to a solution of the alkynyl alcohol from Step 2 (0.90 g, 2.7 mmol) in 6 mL of THF at −40° C. The mix is then warmed to −20° C., stirred for 1 hour, then treated with 10% aq. Rochelle's salt for 2 hours at ambient temperature. The mixture is extracted with ethyl acetate, and the extract is washed with brine, dried over MgSO$_4$, filtered, and evaporated to dryness. The product alkenyl alcohol is purified by silica gel chromatography.

Step 4. A solution of the alkenyl alcohol from Step 3 (3.32 g, 10 mmol) in dichloromethane (15 mL) is treated with 4-methoxybenzyl trichloroacetimidate (4.25 g, 15 mmol) and pyridinium p-toluenesulfonate (0.15 g) for 3 hours at 0° C. The mixture is then warmed to ambient temperature and stirred for 40 hours, then evaporated under vacuum. The product is isolated by flash chromatography on silica gel.

EXAMPLE 10

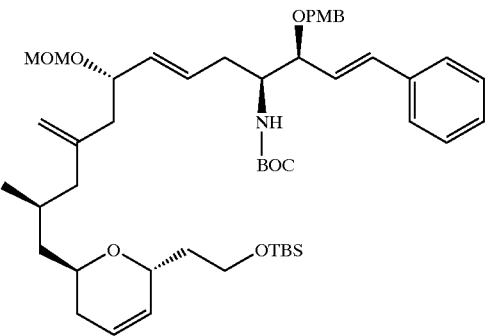

Step 1. A 1.6 M solution of n-butyllithium in hexane (8.0 mL, 13 mmol) is added to a −78° C. solution of (3S,4S)-4-(tert-butoxycarbonylamino)-3-(4-methoxybenzyloxy)-1-phenyl-6-(phenylsulfonyl)-1-hexene (3.48 g, 6.3 mmol) in 60 mL of THF. The mixture is stirred for 15 minutes, and a solution of (2S,6S,8R,12R)-8,12-epoxy-2-(methoxymethoxy)-6-methyl-4-methylidene-14-(tert-butyldimethylsilyloxy)tetradec-10-enal (compound 4 described in Ghosh et al., *J. Org. Chem.* 2001, 66: 8973–8982) (900 mg, 2.05 mmol) is added dropwise. The resulting mixture is warmed to −40° C. and stirred for 2 hours prior to quenching with sat. aq. NH$_4$Cl and extracting with ethyl acetate. The extract is washed with brine, dried over MgSO$_4$, filtered, and evaporated to dryness. The product hydroxy sulfone is purified by silica gel chromatography.

Step 2. A solution of the hydroxysulfone from Step 1 in 30 mL of dichloromethane is treated sequentially with triethylamine (1.0 mL), 4-(dimethylaminopyridine) (50 mg), and acetic anhydride (0.55 mL), and is stirred for 3 hours at ambient temperature. The mixture is washed sequentially with sat. aq. NaHCO$_3$, 1 M NaHSO$_4$, and brine, then dried over MgSO$_4$, filtered, and evaporated to provide the acetate.

Step 3. The acetate from Step 2 is dissolved in methanol (30 mL), cooled to −20° C., and treated with Na$_2$HPO$_4$ (640 mg) followed by 5% w/w sodium amalgam (7.5 g). The resulting suspension is stirred vigorously for 30 minutes, then quenched with sat. NH$_4$Cl and decanted. The liquid is diluted with water and ethyl acetate, and the phases are separated. The organic phase is dried over MgSO$_4$, filtered, and evaporated. Chromatography on silica gel provides the coupled product.

EXAMPLE 11

16,17-desoxylaulimalide lactam

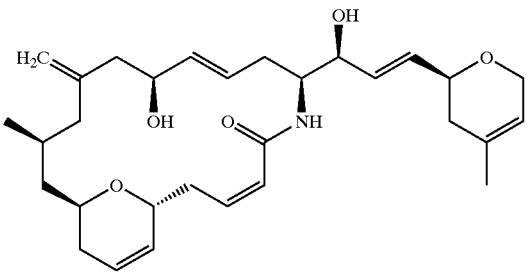

Step 1. A solution of the product of Example 9 (834 mg, 1 mmol) in 10 mL of THF is treated with a 1.0 M solution of tetrabutylammonium fluoride in THF (2.5 mL) for 3 hours at ambient temperature, then quenched with sat. NH$_4$Cl and extracted with ethyl acetate. The organic phase is washed with brine, dried over MgSO$_4$, filtered, and evaporated. Chromatography on silica gel provides the desilylated alcohol.

Step 2. A mixture of the alcohol from Step 1 (720 mg, 1 mmol) and Dess-Martin periodinane (825 mg, 2 mmol) in 25 mL of wet dichloromethane is stirred for 30 minutes, then loaded onto a column of silica gel and chromatographed to provide the aldehyde. In a separate flask, triphenylphosphine (1.17 g) and triethylamine (0.75 mL) are added sequentially to a solution of carbon tetrabromide (0.75 g) in 25 mL of dichloromethane at 0° C., and the solution is stirred for 10 minutes. A solution of the aldehyde in 25 mL of dichloromethane is added dropwise and the mixture is stirred for an additional 30 minutes. The mixture is washed sequentially with sat. aq. NaHCO$_3$, 1 M NaHSO$_4$, and brine, then dried over MgSO$_4$, filtered, and evaporated. Silica gel chromatography provides the dibromide. A solution of the dibromide (874 mg, 1 mmol) in 30 mL of THF at −78° C. is treated with a 1.6 M solution of N-butyllithium in hexane and stirred for 10 minutes. Methyl chloroformate (0.20 mL) is added, and stirring is continued for 30 minutes prior to addition of sat. aq. NH$_4$Cl. The mixture is extracted with ethyl acetate, and the extract is washed with brine, dried over MgSO$_4$, filtered, and evaporated. Silica gel chromatography provides the alkynyl ester.

Step 3. A solution of the alkynyl ester of Step 2 (772 mg, 1 mmol) is dissolved in 1:1 dichloromethane/trifluoroacetic acid (10 mL) at ambient temperature and stirred for 1 hour, then evaporated to dryness. The residue is dissolved in THF (50 mL) and treated with a solution of lithium hydroxide (250 mg) dissolved in 15 mL of water for 2 hours. The mixture is quenched by addition of sat. aq. NH$_4$Cl and extracted with ethyl acetate. The extract is dried over MgSO$_4$, filtered, and evaporated. The residue is dissolved in 100 mL of dichloromethane and treated with 1-[3-(dimethylamino)propyl]-3-ethylcarbodiimide hydrochloride (400 mg) and 1-hydroxybenzotriazole (300 mg) for 24 hours at ambient temperature. The mixture is washed sequentially with 1 N HCl, sat. NaHCO$_3$, and brine, then dried over MgSO$_4$, filtered, and evaporated. The product alkynyl lactam is purified by silica gel chromatography.

Step 4. A mixture of the alkynyl lactam from Step 3 (478 mg, 1 mmol), 1-hexene (80 mL), ethyl acetate (80 mL), and Lindlar catalyst (5% palladium on CaCO$_3$, poisoned with lead; 150 mg) is stirred vigorously under a hydrogen atmosphere for 2 hours. The mixture is filtered through a pad of Celite, which is washed with ethyl acetate. The combined filtrates are evaporated, and the product is purified by silica gel chromatography.

All scientific and patent publications referenced herein are hereby incorporated by reference in their entirety. The invention having now been described, those of skill in the art will recognize that the invention can be practiced in a variety of embodiments, that the description herein is for purposes of illustration and not limitation of the following claims.

What is claimed is:

1. A compound of formula

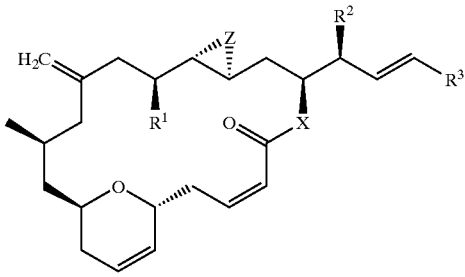

wherein:

X is O or NH;

Z is $CH_2$;

$R^1$ is H, OH, or $C_1$–$C_5$ alkoxy;

$R^2$ is H, OH, or $C_1$–$C_5$ alkoxy; and $R^3$ is cyclohexyl, substituted cyclohexyl, 3-cyclohexenyl, substituted 3-cyclohexenyl, phenyl, substituted phenyl, pyridyl, substituted pyridyl, thiazolyl, substituted thiazolyl, or a group of the formula

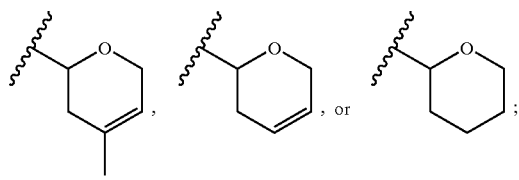

wherein substituted cyclohexyl is cyclohexyl substituted with one or more substituent groups selected from the group consisting of alkyl; alkenyl; alkynyl; aryl; halo; trifluoromethyl; trifluoromethoxy; hydroxy; alkoxy; cycloalkoxy; oxo; alkanoyl; aryloxy; alkanoyloxy; amino; alkylamino; arylamino; aralkylamino; cycloalkylamino; —$NR^4R^5$ in which $R^4$ and $R^5$ are independently selected from alkyl, aryl, or aralkyl; alkanoylamino; aroylamino; aralkanoylamino; mercapto; alkylthio; arylthio; aralkylthio; cycloalkylthio; alkylthiono; arylthiono; aralkylthiono; alkylsulfonyl; arylsulfonyl; aralkylsulfonyl; sulfonamido; nitro; cyano; carboxy; carbamyl; —C(=O)$NR^6R^7$ in which $R^6$ and $R^7$ are independently selected from hydrogen, alkyl, aryl, and aralkyl; alkoxycarbonyl; aryl; guanidino; indoyl; imidazolyl; furyl; thienyl; thiazolyl; pyrrolidyl; pyridyl; pyrimidyl; wherein the substituent groups may optionally be further substituted with halogen, alkyl, alkoxy, aryl, or aralkyl;

substituted 3-cyclohexyl is 3-cyclohexyl substituted with one or more substituent groups selected from the group consisting of alkyl; alkenyl; alkynyl; aryl; halo; trifluoromethyl; trifluoromethoxy; hydroxy; alkoxy; cycloalkoxy; oxo; alkanoyl; aryloxy; alkanoyloxy; amino; alkylamino; arylamino; aralkylamino; cycloalkylamino; —$NR^4R^5$ in which $R^4$ and $R^5$ are independently selected from alkyl, aryl, or aralkyl; alkanoylamino; aroylamino; aralkanoylamino; mercapto; alkylthio; arylthio; aralkylthio; cycloalkylthio; alkylthiono; arylthiono; aralkylthiono; alkylsulfonyl; arylsulfonyl; aralkylsulfonyl; sulfonamido; nitro; cyano; carboxy; carbamyl; —C(=C))$NR^6R^7$ in which $R^6$ and $R^7$ are independently selected from hydrogen, alkyl, and aryl, and aralkyl; alkoxycarbonyl; aryl; guanidino; indoyl; imidazolyl; furyl; thienyl; thiazolyl; pyrrolidyl; pyridyl; pyrimidyl; wherein the substituent groups may optionally be further substituted with halogen, alkyl, alkoxy, aryl, or aralkyl;

substituted phenyl is phenyl substituted with one or more substituent groups selected from the group consisting of alkyl; alkenyl; alkynyl; aryl; halo; trifluoromethyl; trifluoromethoxy; hydroxy; alkoxy; cycloalkoxy; oxo; alkanoyl; aryloxy; alkanoyloxy; amino; alkylamino; arylamino; aralkylamino; cycloalkylamino; —$NR^4R^5$ in which $R^4$ and $R^5$ are independently selected from alkyl, aryl, or aralkyl; alkanoylamino; aroylamino; aralkanoylamino; mercapto; alkylthio; arylthio; aralkylthio; cycloalkylthio; alkylthiono; arylthiono; aralkylthiono; alkylsulfonyl; arylsulfonyl; aralkylsulfonyl; sulfonamido; nitro; cyano; carboxy; carbamyl; —C(=O)$NR^6R^7$ in which $R^6$ and $R^7$ are independently selected from hydrogen, alkyl, aryl, and aralkyl; alkoxycarbonyl; aryl; guanidino; indoyl; imidazolyl; furyl; thienyl; thiazolyl; pyrrolidyl; pyridyl; pyrimidyl; wherein the substituent groups may optionally be further substituted with halogen, alkyl, alkoxy, aryl, or aralkyl;

substituted pyridyl is pyridyl substituted with one or more substituent groups selected from the group consisting of alkyl; alkenyl; alkynyl; aryl; halo; trifluoromethyl; trifluoromethoxy; hydroxy; alkoxy; cycloalkoxy; oxo; alkanoyl; aryloxy; alkanoyloxy; amino; alkylamino; arylamino; aralkylamino; cycloalkylamino; —$NR^4R^5$ in which $R^4$ and $R^5$ are independently selected from alkyl, aryl, or aralkyl; alkanoylamino; aroylamino; aralkanoylamino; mercapto; alkylthio; arylthio; aralkylthio; cycloalkylthio; alkylthiono; arylthiono; aralkylthiono; alkylsulfonyl; arylsulfonyl; aralkylsulfonyl; sulfonamido; nitro; cyano; carboxy; carbamyl; —C(=O)$NR^6R^7$ in which $R^6$ and $R^7$ are independently selected from hydrogen, alkyl, aryl, and aralkyl; alkoxycarbonyl; aryl; guanidino; indoyl; imidazolyl; furyl; thienyl; thiazolyl; pyrrolidyl; pyridyl; pyrimidyl; wherein the substituent groups may optionally be further substituted with halogen, alkyl, alkoxy, aryl, or aralkyl;

substituted thiazoyl is thiazoyl substituted with one or more substituent groups selected from the group consisting of alkyl; alkenyl; alkynyl; aryl; halo; trifluoromethyl; trifluoromethoxy; hydroxy; alkoxy; cycloalkoxy; oxo; alkanoyl; aryloxy; alkanoyloxy; amino; alkylamino; arylamino; aralkylamino; cycloalkylamino; —$NR^4N^5$ in which $R^4$ and $R^5$ are independently selected from alkyl, aryl, or aralkyl; alkanoylamino; aroylamino; aralkanoylamino; mercapto; alkylthio; arylthio; aralkylthio; cycloalkylthio; alkylthiono; arylthiono; aralkylthiono; alkylsulfonyl; arylsulfonyl; aralkylsulfonyl; sulfonamido; nitro; cyano; carboxy; carbamyl; —C(=O)$NR^6 R^7$ in which $R^6$ and $R^7$ are independently selected from hydrogen, alkyl, aryl, and aralkyl; alkoxycarbonyl; aryl; guanidino; indoyl; imidazolyl; furyl; thienyl; thiazolyl; pyrrolidyl; pyridyl; pyrimidyl; wherein the substituent groups may optionally be further substituted with halogen, alkyl, alkoxy, aryl, or aralkyl.

2. A compound of claim 1 wherein $R^1$ is OH, or $C_1$–$C_5$ alkoxy.

* * * * *